United States Patent
Al-Jazaeri

(10) Patent No.: US 10,500,331 B2
(45) Date of Patent: Dec. 10, 2019

(54) DRAINAGE CATHETER WITH RETRACTABLE INTERNAL DRAINS

(71) Applicant: Ayman H. Al-Jazaeri, Riyadh (SA)

(72) Inventor: Ayman H. Al-Jazaeri, Riyadh (SA)

( * ) Notice: Subject to any disclaimer, the term of this patent is extended or adjusted under 35 U.S.C. 154(b) by 215 days.

(21) Appl. No.: 15/680,491

(22) Filed: Aug. 18, 2017

(65) Prior Publication Data

US 2019/0054230 A1    Feb. 21, 2019

(51) Int. Cl.
| | |
|---|---|
| A61M 3/02 | (2006.01) |
| A61M 1/28 | (2006.01) |
| A61M 25/00 | (2006.01) |
| A61M 27/00 | (2006.01) |
| A61M 25/01 | (2006.01) |
| A61M 25/09 | (2006.01) |

(52) U.S. Cl.
CPC .......... *A61M 3/0283* (2013.01); *A61M 1/285* (2013.01); *A61M 25/007* (2013.01); *A61M 25/0026* (2013.01); *A61M 25/0082* (2013.01); *A61M 27/00* (2013.01); *A61M 27/006* (2013.01); *A61M 25/0071* (2013.01); *A61M 25/0102* (2013.01); *A61M 25/09* (2013.01); *A61M 2025/0096* (2013.01); *A61M 2025/0175* (2013.01); *A61M 2205/583* (2013.01)

(58) Field of Classification Search
CPC ............ A61M 3/0283; A61M 25/0026; A61M 25/0071; A61M 27/00; A61M 27/006; A61M 2025/0175; A61M 25/007; A61M 25/0102; A61M 2005/311
See application file for complete search history.

(56) References Cited

U.S. PATENT DOCUMENTS

| | | |
|---|---|---|
| 3,753,439 A | 8/1973 | Brugarolas |
| 4,351,333 A | 9/1982 | Lazarus |
| 4,368,737 A | 1/1983 | Ash |
| 4,377,169 A | 3/1983 | Banks |
| 4,681,570 A | 7/1987 | Dalton |
| 4,767,400 A | 8/1988 | Miller |
| 4,925,452 A | 5/1990 | Melinyshyn |
| 5,100,395 A | 3/1992 | Rosenberg |
| 5,116,310 A | 5/1992 | Seder |

(Continued)

FOREIGN PATENT DOCUMENTS

WO    WO 2003030960    4/2003

*Primary Examiner* — Nilay J Shah
(74) *Attorney, Agent, or Firm* — Neustel Law Offices

(57) ABSTRACT

A drainage catheter with retractable internal drains for fluid drainage and irrigation includes a primary catheter for insertion within a subject, a lumen within the primary catheter for conducting fluid flow between a source of fluid drainage or irrigation and the subject, and a plurality of selectively retractable and deployable drains in fluid communication with the lumen. Retraction and deployment of the drains within a subject is accomplished remotely via a specially shaped stylet and common drain connector within the primary catheter. The plurality of drains are enclosed within the primary catheter in the retracted state and extend radially outwardly from the primary catheter in the deployed state. In the retracted state, insertion and location of the primary catheter in a subject are facilitated. In the deployed state, expanded and improved drainage and irrigation area and a plurality of fluid flow paths and locations are provided.

31 Claims, 9 Drawing Sheets

(56) References Cited

U.S. PATENT DOCUMENTS

| | | | |
|---|---|---|---|
| 5,254,084 A | 10/1993 | Geary | |
| 5,354,279 A * | 10/1994 | Hofling | A61M 25/0069 |
| | | | 604/164.12 |
| 5,370,610 A | 12/1994 | Reynolds | |
| 5,800,414 A | 9/1998 | Cazal | |
| 5,891,111 A | 4/1999 | Ismael | |
| 6,231,570 B1 | 5/2001 | Tu | |
| 6,913,589 B2 | 7/2005 | Dextradeur | |
| 6,961,602 B2 | 11/2005 | Fuimaono | |
| 7,366,557 B2 | 4/2008 | Bautista | |
| 7,763,142 B2 | 7/2010 | Watson | |
| 8,066,697 B2 | 11/2011 | Zvuloni | |
| 8,221,393 B1 | 7/2012 | Placik | |
| 8,409,171 B2 | 4/2013 | Hannon | |
| 8,827,944 B2 | 9/2014 | Sevrain | |
| 8,920,404 B2 | 12/2014 | Difiore | |
| 9,248,254 B2 * | 2/2016 | Dehnad | A61L 31/16 |
| 9,314,299 B2 | 4/2016 | Fang | |
| 2003/0135147 A1 | 7/2003 | Rosenberg | |
| 2008/0033396 A1 | 2/2008 | Danek | |
| 2010/0305509 A1 | 12/2010 | Osypka | |
| 2012/0078159 A1 | 3/2012 | Wilson | |
| 2012/0179144 A1 | 7/2012 | Carleo | |
| 2012/0323175 A1 * | 12/2012 | Vogelbaum | A61M 25/0054 |
| | | | 604/95.04 |
| 2014/0058315 A1 | 2/2014 | Gupta | |
| 2014/0163532 A1 | 6/2014 | Cornet | |

* cited by examiner

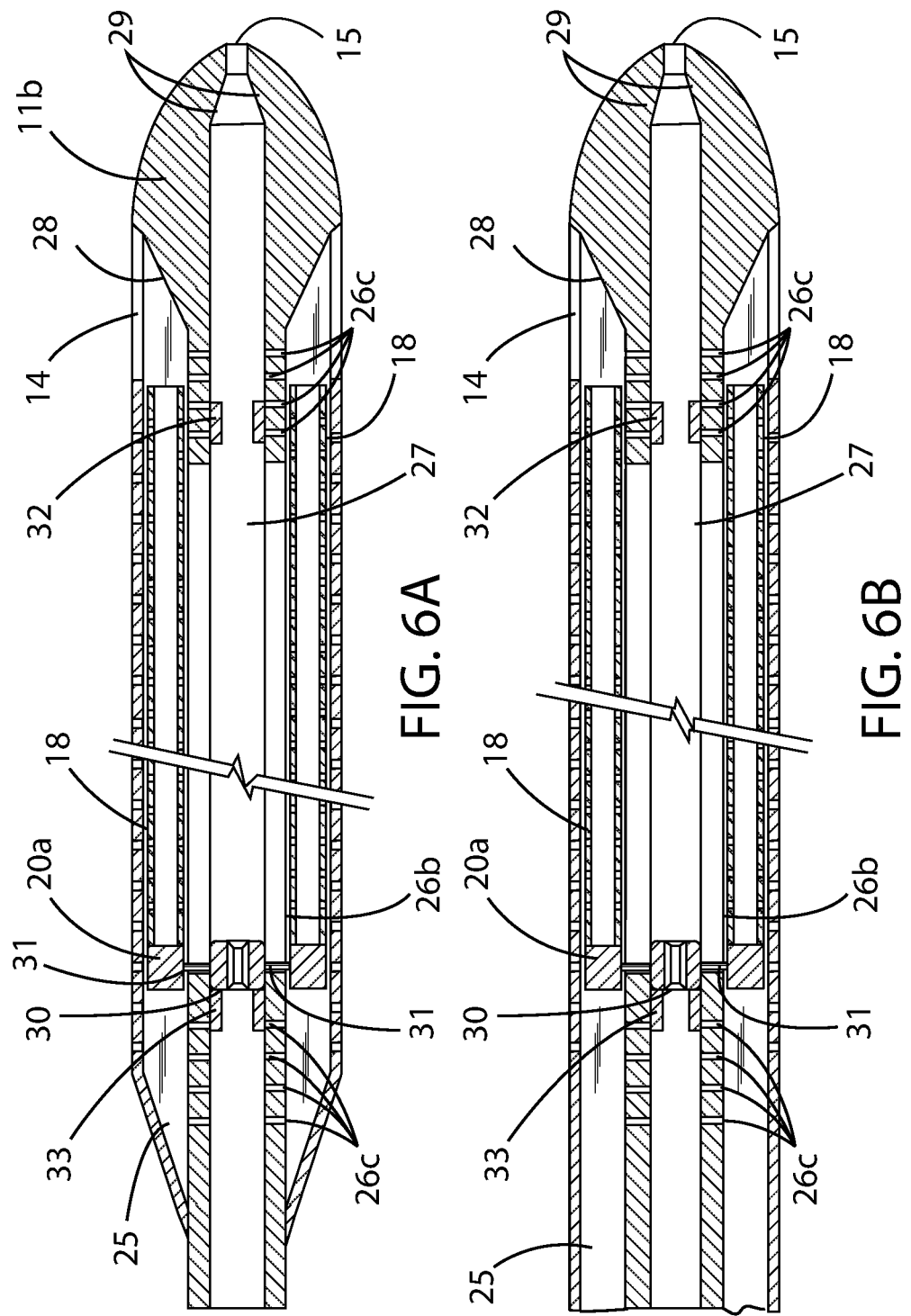

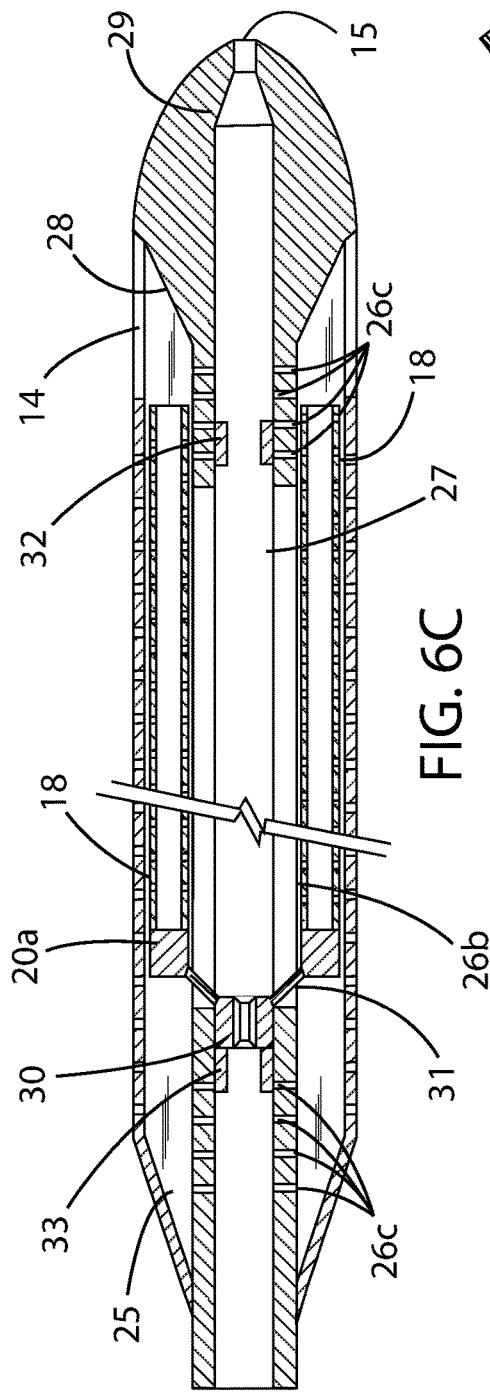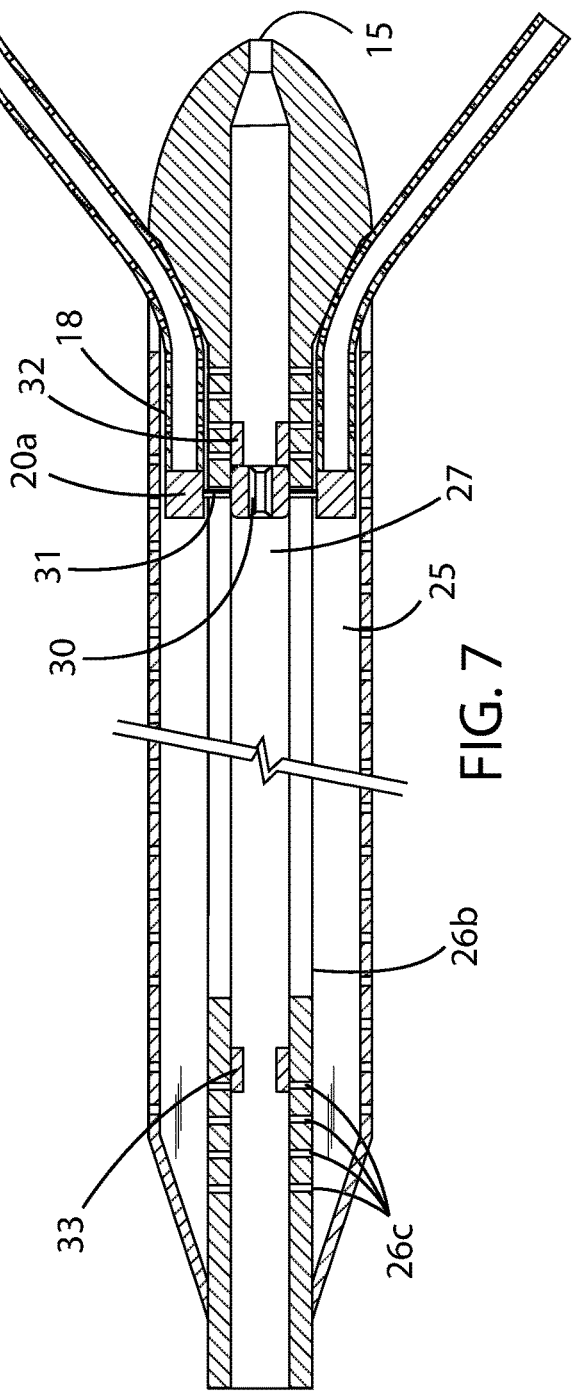

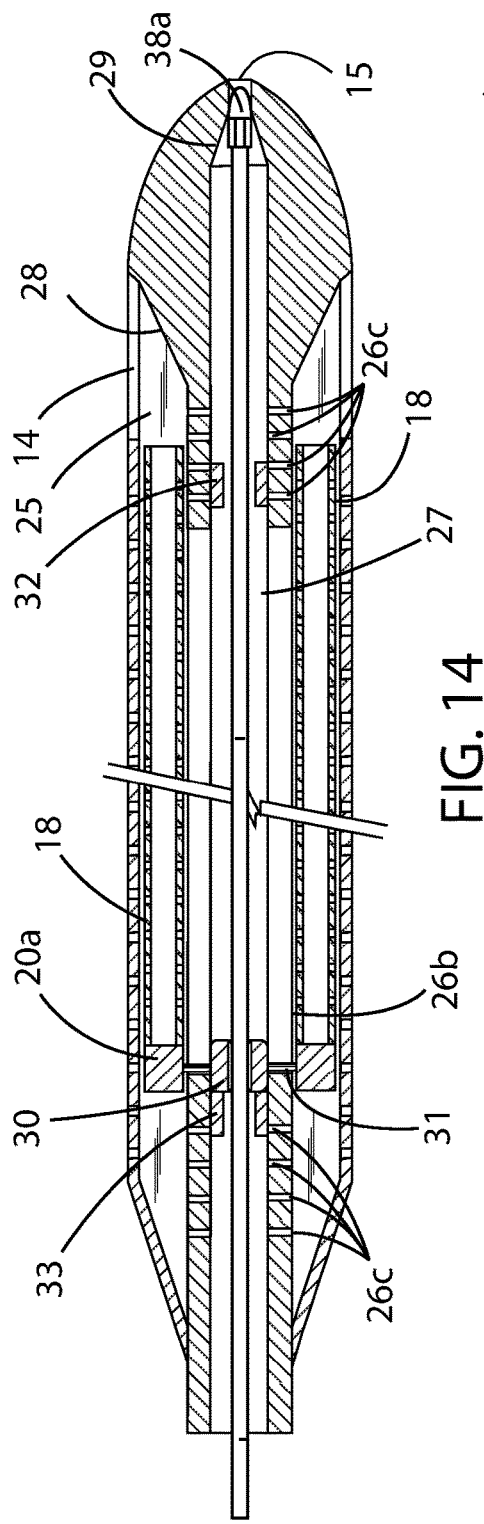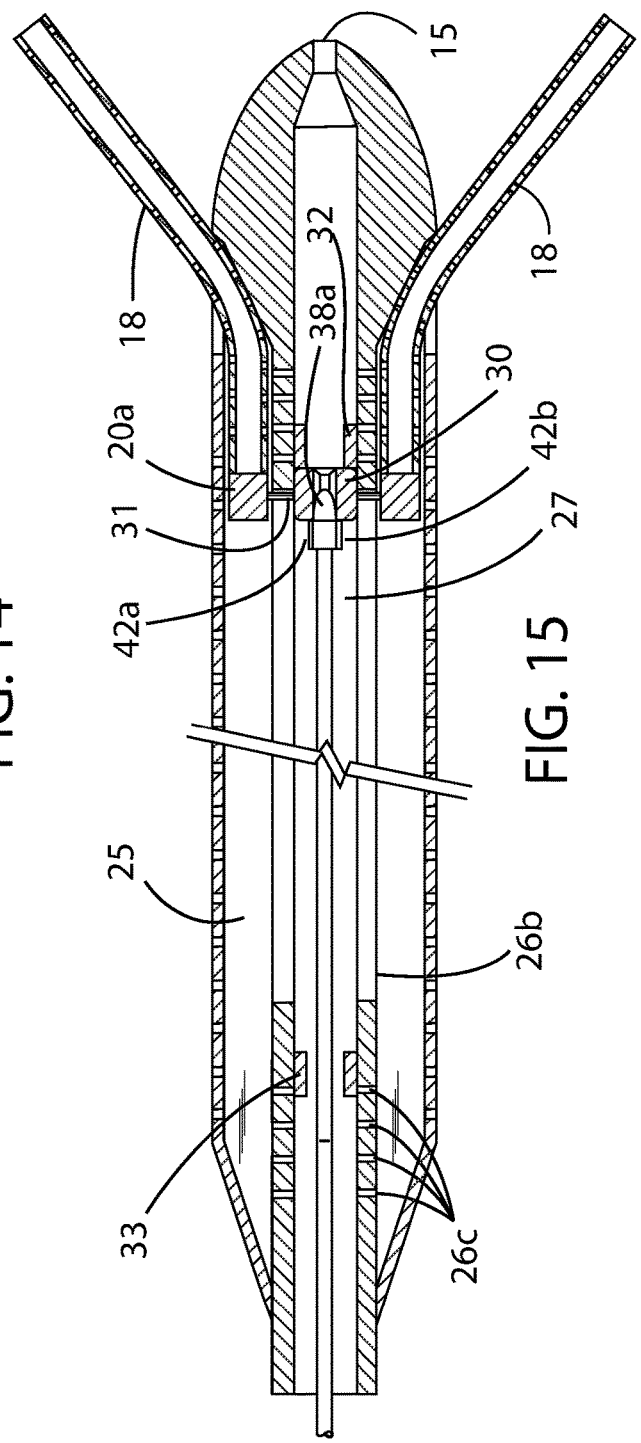
FIG. 14
FIG. 15

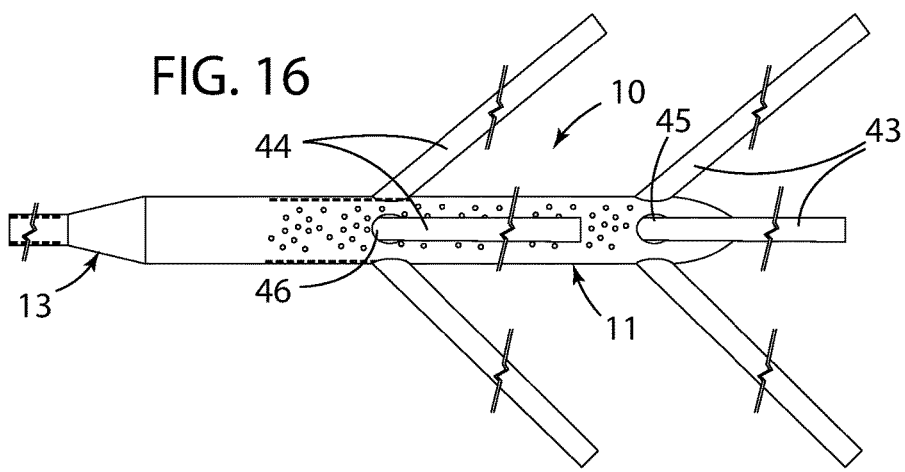
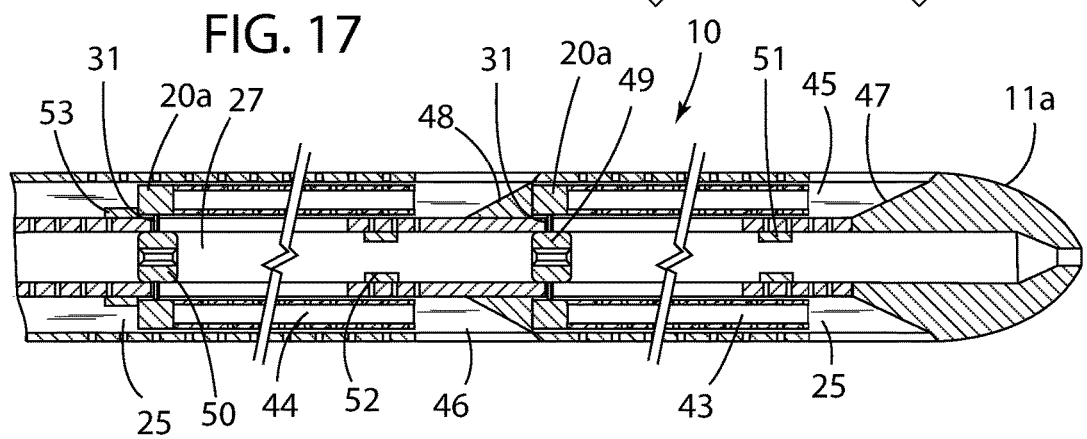
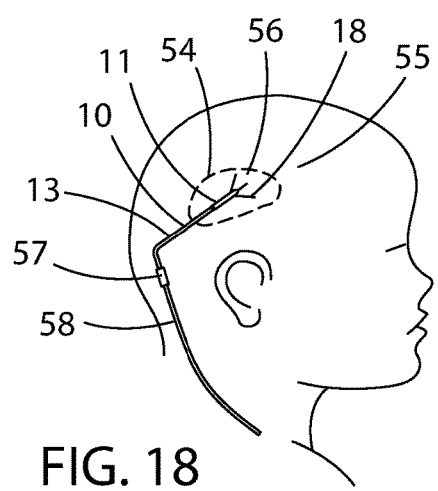
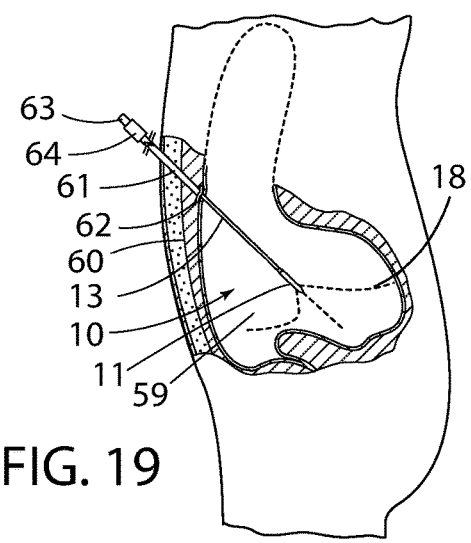

DRAINAGE CATHETER WITH RETRACTABLE INTERNAL DRAINS

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND

Field

Example embodiments in general relate to a Drainage Catheter With Retractable Internal Drains for providing improved fluid drainage and irrigation particularly for medical applications.

Related Art

Any discussion of the related art throughout the specification should in no way be considered as an admission that such related art is widely known or forms part of common general knowledge in the field.

Draining fluid from the body of a subject may be necessary for treating various illnesses. Excessive body fluid can accumulate causing unwanted symptoms or complications. For example, excess accumulation of cerebrospinal fluid can lead to hydrocephalus, excess accumulation of plural fluid can cause pleural effusion, and excess accumulation of peritoneal fluid can cause ascites. Other fluids that might require drainage include infected fluid in abscesses or blood in hematomas.

In other cases, it may be necessary or desirable to artificially introduce fluid into a subject's body from outside to provide irrigation or to washout body wastes. For example, in patients with renal failure peritoneal dialysis is regularly performed by artificially introducing a dialysis fluid from outside a subject's body into the subject's abdomen via a special catheter, and then draining fluid from the subject's body, washing out accumulated wastes and salts in the process.

A problem facing most body fluid drainage catheters is frequent blockage of the catheter. This problem is typically addressed with simple procedures such as flushing or manual manipulation. However, on many occasions these procedures fail and replacement of the catheter becomes necessary. Catheter replacement can be simple, though uncomfortable, such as in the case of urinary catheter replacement, or it can be complex and require an operative procedure, such as in the cases of cerebrospinal fluid shunt replacement or peritoneal dialysis catheter replacement.

Drainage catheter blockage is frequently attributed to clogged catheter pores or clogged drainage lumens. Typical causes include thick debris in the drained fluid, as in the case of pus drainage, or clotted blood as in the case of hematoma drainage. In other instances, such as when an indwelling catheter is left in situ for a long time, cavity endogenous tissues can coat the catheter's outer surface effectively blocking it from the surrounding fluid to be drained. This condition can arise in connection with peritoneal drainage for example. The tissues of a cavity being drained can even grow inside or through the drainage holes/pores of the catheter. For example, this condition can manifest in connection with a cerebrospinal fluid drainage catheter or when the inflow portion of a ventriculoperitoneal shunt is blocked by the ingrowth of the choroid plexus.

Another challenge with drainage and irrigation catheterization is that in many instances multiple or larger fluid-filled cavities or areas need to be drained or washed at the same time. This can be the case when dealing with multiple abdominal collections or pockets of pus, or after surgery that includes bowel, biliary or urinary tract anastomosis (connection). In other instances, a single cavity or tract may branch into multiple tracts that require drainage simultaneously, such as in the case of the bladder and ureters, the biliary tree, and blood vessels. The traditional approach to drain multiple or larger cavities or areas simultaneously has been to place a separate drainage catheter in each cavity or space through a natural anatomical opening and small incisions, or to use a wider incision to insert multiple catheters.

A number of catheter designs have been proposed in an attempt to address the foregoing problems and challenges. For example, it has been proposed to join together a plurality of individual elongated open-ended tube structures to form a catheter structure. In the proposed designs, the distal ends of the tube structures are spaced apart from each other and distributed within a cavity to be drained. The proximal ends of the tube structures are adapted to be connected to a drainage bag, cannula, or other drainage collection point or source of irrigation fluid. The number and spaced apart distribution of the distal tube structures increases the drainage area, and provides multiple drainage locations and fluid flow paths. See, for example, U.S. Pat. Nos. 5,891,111 and 5,800,414. Similar multi-tube drainage catheters have been proposed in which the proximal ends of the tube structures converge into a common tubular drain structure. See, for example, U.S. Pat. Nos. 4,377,169; 5,100,395; 8,221,393; 4,925,452; 8,221,393; and 6,913,589; and Published U.S Patent Application No. 2014/0163532 A1. U.S. Pat. No. 6,691,602 similarly discloses a catheter comprising a catheter body with a single central lumen and a plurality of spines extending radially outward from a distal end. Each of the spines carries an electrode utilized for mapping and location sensing functionalities.

The foregoing multi-drain catheters suffer from a variety of problems and shortcomings. For example, because the proposed catheters have multiple distal drain ducts and drain tubes fixed in a permanently deployed state they occupy a relatively large volume of space. This makes insertion in a subject difficult. Insertion through an incision is likely to require a relatively large incision, which can be more problematic for the subject. Alternatively, insertion through a naturally occurring tract of a subject may be difficult or impossible due to the length and narrowness of the tract. For example, it may be difficult or impossible to insert such a catheter into the stomach of a subject through the subject's nose or mouth tract, as in the case of a nasogastric tube, or through a subject's urethra, as in the case of a Foley catheter. Further, such a catheter is likely incapable of deep percutaneous insertion as the plurality of permanently deployed distal drain tubes is likely to create significant friction while advancing through long narrow tracts and to encounter obstructions when passing through a subject's tissues.

One proposed multi-tube catheter described in Published U.S. Patent Application No. 2014/0058315 A1 attempts to address the foregoing insertion problems. The proposed catheter, which is intended for use in continuous flow peritoneal dialysis, has an inflow tube and an outflow tube. The inflow and outflow tubes are divided at their distal ends into a plurality of smaller inflow and outflow tubes with apertures along their lengths for the inflow and outflow of dialysis solution. An insertion sheath covers the plurality of smaller inflow and outflow tubes during insertion. The proximal and distal ends of the plurality of smaller inflow and outflow tubes are joined together so that when the insertion sheath is retracted following insertion the distal tubes deploy into an open-basket shape in the peritoneal cavity.

Although the proposed catheter addresses the insertion difficulties of other multi-tube catheters by enclosing the plurality of tube structures in a sheath during insertion, the plurality of tube structures are joined at their distal ends and the catheter is therefore incapable of providing multiple spaced apart drain locations or locating drain tubes in different spaces like the other proposed multi-tube catheters. Moreover, deployment of the distal tube structures in an "open basket" configuration creates a risk of entangling or entrapping a subject's internal organs or a section of bowel during or after deployment.

Published U.S. Patent Application No. 2012/0179144 discloses a similar catheter, however, having only a single drain. The catheter comprises an elongated member enclosed by a sleeve. The elongated member has an interior lumen, drainage openings near a distal end, and a funnel at a proximal end. The sleeve is co-axial with the elongated member and is retractable. During insertion, the distal end of the elongated member is enclosed within the sleeve. After the catheter is inserted, the sleeve is retracted so that the distal end of the elongated member is exposed outside the sleeve to provide drainage. When the drainage procedure is completed, the sleeve may be extended to again enclose the distal end of the elongated member. However, because the catheter has only a single internal drain it is only capable of providing a single point of drainage at a single location.

U.S. Pat. No. 6,231,570 also discloses a similar catheter, but for the delivery of electrodes for tissue ablation rather than for drainage or irrigation. The catheter includes an elongated delivery catheter that encloses a plurality of inner micro-catheters within tracks. A handle at a proximal end of the delivery catheter is provided with a push-pull deployment mechanism for extending and retracting the micro-catheters out of and into a distal end of the delivery catheter. The micro-catheters comprise electrodes for use in tissue ablation.

Another multi-lumen catheter proposed by Published U.S. Patent Application No. 2012/0078159 A1 also attempts to address problems connected with insertion in a subject. The proposed catheter is a ventricular catheter having an elongated catheter body. Enclosed within the catheter body are a plurality of fixed lumens at a distal end and a single fixed lumen at a proximal end. A plurality of slits in the catheter body corresponding to the plurality of distal lumens allows fluid to enter the distal lumens and flow to the single proximal lumen for extraction. While the proposed ventricular catheter addresses the insertion problems of other prior art multi-drain catheters by reducing the space occupied by the multiple distal lumens, it provides only very limited drainage surface area and lacks the ability to provide multiple spaced apart drainage locations like other proposed multi-drain catheters.

Other proposals have been made to permit the insertion of catheters into subjects through smaller incisions, including using insertion sheaths, lumens constructed of collapsible materials, etc. See, for example Published U.S. Patent Application Nos. 2008/0033396 A1 and 2010/0305509 A1; and U.S. Pat. No. 4,351,333. However, these proposals also suffer from various problems and shortcomings. For example, some require additional tools while others require additional steps, both complicating the insertion process. Additionally, using an insertion sheath still may not adequately address the problems that attend inserting a multi-drain catheter having a plurality of distal drain tubes. The distal tubes of such catheters may still occupy so much space that they encounter excess friction or obstructions even while passing through a sheath. Such catheters with smaller internal drain lumens may even bend, making insertion even more difficult, particularly when the insertion length is long and/or the insertion tract has twists and turns. Still further, none of the proposals address how to insert and direct the distal drain tubes of a multi-drain catheter within a sheath into different areas to be drained, or how to advance the drain tubes further or direct them into different locations once the sheath is removed.

Yet other catheter designs have been proposed to increase the drainage surface area to address the blockage problems frequently encountered. For example, U.S. Pat. No. 4,368,737 proposed a catheter with a sheet-like distal tip. U.S. Pat. No. 5,254,084 proposed a catheter having multiple distal tips enclosed in an envelope. Published International Application WO2003030960 proposed a catheter with a coiled distal tip. U.S. Pat. No. 4,681,570 and Published U.S. Patent Application No. 2003/0135147 A1 proposed a catheter with a distal tip in a cylindrical helix or coil configuration. However, all of these designs still present the same insertion problems as the multi-drain catheter designs. Moreover, they are only capable of draining a single area at a time and cannot provide multiple drain sites in different locations simultaneously and without multiple insertions.

Still other catheter designs have been proposed employing various materials to address the catheter clogging and blocking problem. U.S. Pat. No. 4,767,400 proposed a catheter with a plurality of very fine pores at the distal tip. U.S. Pat. Nos. 8,827,944 and 7,763,142 proposed catheters comprising semi-permeable or permeable membranes. U.S. Pat. No. 3,743,439 proposed covering the distal tip with certain padding material. However, none of the proposed designs has successfully solved the problems of catheter clogging by fluid borne debris and the coating of indwelling catheters by endogenous tissue. Moreover, the presence of fabric or netted materials can harbor bacteria and lead to infection, and the inclusion of padding material can require a larger entry wound for insertion.

From the foregoing, it can be seen that while a variety of catheter designs have been proposed, the disclosed catheters remain subject to various problems and shortcomings. There remains a need for a catheter that provides increased surface area to enhance drainage rate and reduce the risk of blockage of the catheter drainage ports by fluid debris and/or tissue ingrowth. There also remains a need for such a catheter that can be inserted into a subject percutaneously and through body tissues through a relatively small incision, or through long narrow natural tracts of a subject, such as the digestive and urinary tracts, without causing excessive friction or being prone to obstructions. There further is a need for such a catheter that can be inserted in a location within a subject to provide drainage or irrigation in that location, and that at the same time can provide drainage or irrigation in other locations within the subject without the need to separately insert additional catheters. There further is a need for such a catheter with multiple internal drains and that can selectively and independently provide multiple-distal drains in multiple locations within a subject at the same time and without requiring separate insertion of multiple catheters.

The example embodiments of a drainage catheter with retractable internal drains disclosed herein are directed to addressing the foregoing needs and the foregoing and other problems and shortcomings of the prior art.

SUMMARY

An example embodiment is directed to a drainage catheter with retractable internal drains. The drainage catheter with retractable internal drains includes a primary catheter adapted for insertion within a subject, at least one lumen within the primary catheter for conducting fluid flow between a source of fluid drainage or irrigation and the subject, a plurality of drain ports in the primary catheter and a plurality of selectively retractable and deployable drains in fluid communication with the lumen. The plurality of drains, which can take the form of elongated open-ended tubes, are enclosed within the primary catheter in the retracted state and extend radially outwardly from the primary catheter through the drain ports in the deployed state. In some embodiments, the primary catheter includes a plurality of lumens for conducting fluid flow between the proximal and distal ends and the plurality of drains are enclosed within at least some of the plurality of lumens in the retracted state.

In another example embodiment, two or more sets of longitudinally spaced drain ports and selectively retractable and deployable drains are provided. The two or more sets of drains are independently retractable and deployable and are enclosed within the primary catheter in the retracted state and extend radially outwardly from the primary catheter through the two or more sets of drain ports in the deployed state.

A common aspect of the example embodiments is that in the retracted state of the drains, insertion and location of the primary catheter in a subject are facilitated. In the deployed state of the drains, expanded drainage and irrigation area and a plurality of fluid flow paths and locations are provided.

There has thus been outlined, rather broadly, some of the embodiments of the drainage catheter with retractable internal drains in order that the detailed description thereof may be better understood, and in order that the present contribution to the art may be better appreciated. There are additional embodiments of the drainage catheter with retractable internal drains that will be described hereinafter and that will form the subject matter of the claims appended hereto. In this respect, before explaining at least one embodiment of the drainage catheter with retractable internal drains in detail, it is to be understood that the drainage catheter with retractable internal drains is not limited in its application to the details of construction or to the arrangements of the components set forth in the following description or illustrated in the drawings. The drainage catheter with retractable internal drains is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 6A is a partial longitudinal cross-sectional side view of a drainage catheter with retractable internal drains in accordance with an example embodiment.

FIG. 6B is a partial longitudinal cross-sectional side view of a drainage catheter with retractable internal drains in accordance with another example embodiment.

FIG. 6C is a partial longitudinal cross-sectional side view of a drainage catheter with retractable internal drains in accordance with yet another example embodiment.

FIG. 7 is a partial longitudinal cross-sectional side view of a drainage catheter with retractable internal drains in accordance with an example embodiment with drain tubes in a deployed position.

FIG. 14 is a partial longitudinal cross-sectional side view of a primary catheter of a drainage catheter with retractable internal drains in accordance with an example embodiment with the distal tip of the stylet in engagement with the distal tip of the primary catheter and drain tubes in a retracted position.

FIG. 15 is a partial longitudinal cross-sectional side view of a primary catheter of a drainage catheter with retractable internal drains in accordance with an example embodiment with drain tubes in a deployed position.

FIG. 16 is a partial side view of a drainage catheter with retractable internal drains in accordance with another example embodiment with two sets of drain tubes in deployed position.

FIG. 17 is a partial longitudinal cross-sectional side view of a drainage catheter with retractable internal drains in accordance with another example embodiment with two sets of drain tubes in retracted position.

FIG. 18 is a partial side cutaway view of a drainage catheter with retractable internal drains in accordance with an example embodiment implanted within a ventricle of a subject and integrated with a ventriculoperitoneal shunt system.

FIG. 19 is a partial side cutaway view of a drainage catheter with retractable internal drains in accordance with an example embodiment implanted within a peritoneal cavity of a subject and integrated with a peritoneal dialysis system.

DETAILED DESCRIPTION

A. Overview.

An example drainage catheter with retractable internal drains generally includes a primary catheter, a plurality of internal retractable drains, a central connecting piece, and a stylet adapted to engage with the central connecting piece. The primary catheter comprises proximal and distal ends and has a plurality of drain openings therebetween. A plurality of internal drain ports are formed in the distal end of the catheter body. A central track and a plurality of peripheral tracks within the primary catheter define a plurality of lumens which are adapted to conduct fluid flow between the proximal and distal ends of the catheter for drainage and irrigation.

An internal retractable drain is disposed within each of the peripheral tracks. During insertion of the primary catheter into a subject, the internal drains are in a retracted state within the peripheral tracks. After insertion, the internal retractable drains can be repositioned in a deployed state in which they extend radially outwardly from the catheter body through the plurality of internal drain ports. In the deployed state, the internal retractable drains can be directed to a plurality of locations within the subject to increase the drainage or irrigation area, provide drainage and irrigation to a plurality of locations within the subject simultaneously, and provide a plurality of fluid flow paths to reduce or prevent blockage.

A central connecting piece is disposed within the central track of the primary catheter body, is connected in common with the plurality of internal retractable drains, and is adapted to slide within the central track. By causing the central connecting piece to slide within the central track, the plurality of internal retractable drains are correspondingly caused to slide within their respective peripheral tracks between the retracted and deployed positions.

The central connecting piece operates in conjunction with an elongated stylet having a distal tip to insert and locate the primary catheter within a patient and to selectively deploy and retract the internal retractable drains. In one angular orientation of the stylet, the distal tip passes through the central connecting piece and engages the distal end of the primary catheter for insertion of the primary catheter in a subject. In another angular orientation, the distal tip engages the central connecting piece causing it to slide in the central track to deploy or retract the internal retractable drains.

In one example embodiment, the primary catheter has multiple sets of internal retractable drains and multiple sets of corresponding internal drain ports. In this embodiment, each set of internal retractable drains has a corresponding central connecting piece and each set is independently deployable and retractable using the stylet.

B. Primary Catheter.

Figure 1:
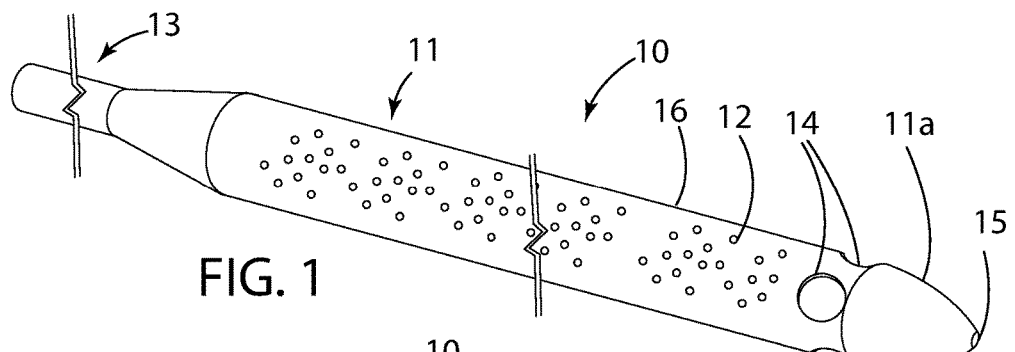
FIG. 1 is a perspective view of a drainage catheter with retractable internal drains in accordance with an example embodiment.
Figure 2:
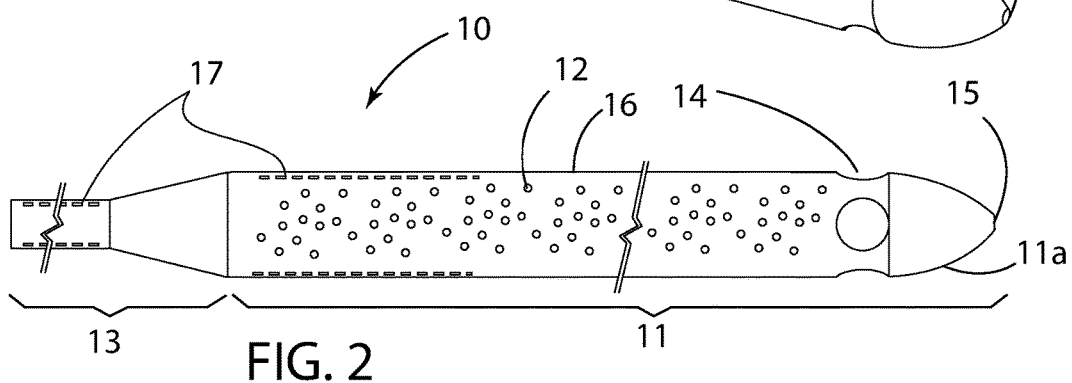
FIG. 2 is a partial side view of a drainage catheter with retractable internal drains in accordance with an example embodiment.

Referring to FIGS. 1 and 2, one example embodiment of a drainage catheter with retractable internal drains comprises a primary catheter 10 having a catheter body or housing 16. The primary catheter is typically though not necessarily formed in an elongated cylindrical shape to facilitate insertion and location within a subject. However, other shapes known to persons skilled in the art may also be used depending on the particular intended application. Persons skilled in the art also will appreciate that the primary catheter may be constructed within a range of length and diameter dimensions depending on the intended application, the anatomy of a subject to be catheterized, the desired drainage and irrigation performance, and other considerations. The primary catheter is ideally formed of a flexible material such as polyurethane or medical silicon, but other materials suitable for use in catheter applications will also be known to persons of ordinary skill in the art and may be used.

The primary catheter 10 has a proximal end 13 and a distal end 11 with a distal end tip 11a. A plurality of relatively small drain openings 12 are preferably formed in the catheter body 16 at the distal end by suitable means to conduct fluid flow between the exterior and interior of the catheter body. The proximal end is ideally but not necessarily smaller in diameter than the distal end and preferably has a fluid impermeable surface. The primary function of the proximal end is to connect the catheter to drainage or irrigation tubes, containers, and the like. Accordingly, the proximal end terminates in an opening (not shown) for conducting fluid flow into and out of the primary catheter.

At least one and preferably multiple internal drain ports 14 are formed in the distal end near the distal end tip. The internal drain ports 14 are sized relatively larger than the drain openings 12 to accommodate a corresponding number of internal retractable drains 18, as will be described in detail below. As also described further below, a plurality of internal drain ports 14 preferably are arranged radially around the circumference of the distal end spaced slightly inwardly (proximally) from the distal end tip. Also preferably, a guidewire port 15 is formed centrally in the distal end tip 11a to permit a guidewire (not shown) to be inserted and to pass through the primary catheter between the distal end tip 11a and the proximal end 13. A guidewire may be preinserted into a space within a subject desired to be drained, for example using a hollow needle under radiological image guidance. The primary catheter may then be slid over the guidewire to guide it into the space desired to be drained.

A plurality of orientation indicators 17 are also formed in the catheter body 16. Preferably, a first plurality of orientation indicators are formed in the proximal end 13 and a second plurality of orientation indicators are formed in the distal end 11. However, in some embodiments, even a single orientation indicator formed in either the proximal or distal end may be suitable. The orientation indicators preferably comprise longitudinal slits formed in radially opposed sides of the catheter body 16. The slits may extend through the catheter body if desired and may also extend along its entire length if desired. The slits provide a visual indication to assist in angularly orienting a stylet 36 with respect to a central connecting piece 30 within the primary catheter in a manner and for a purpose to be described in detail below.

Referring now primarily to FIGS. 6A-6C, 8, and 11-13, the interior of the primary catheter includes a central track 27 and a plurality of peripheral tracks 25. The central track 27 defines a central lumen and the plurality of peripheral tracks 25 define a corresponding plurality of peripheral lumens adapted to conduct fluid flow between the distal and proximal ends of the primary catheter. The peripheral tracks and lumens preferably are radially spaced circumferentially about the central track and lumen.

Figures 8, 9, 9A, 9B:
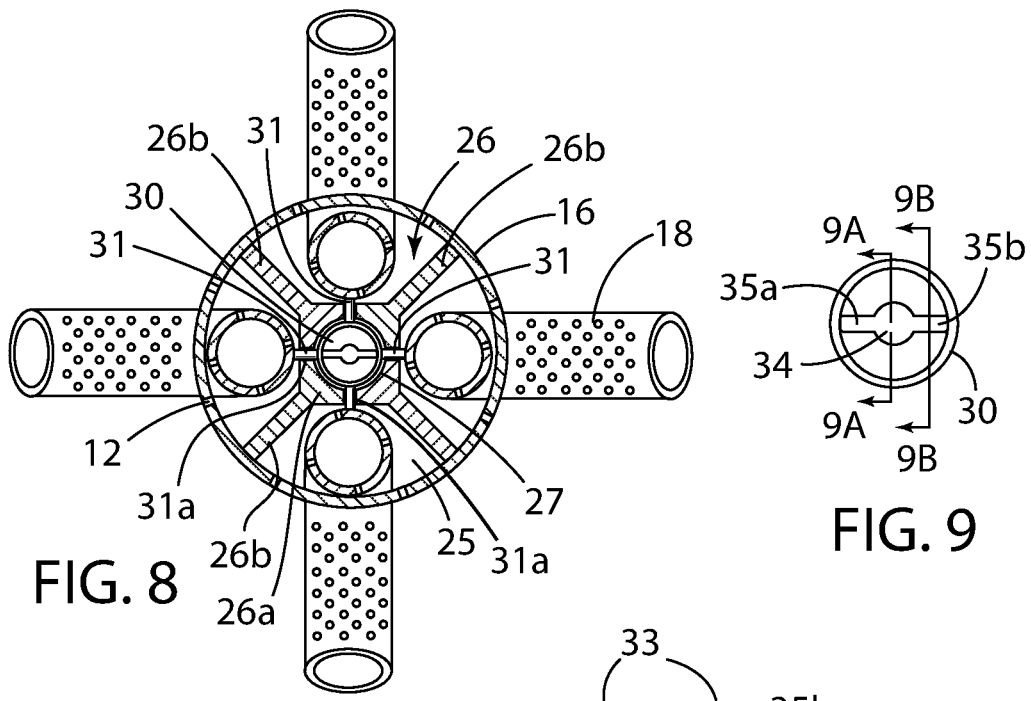
FIG. 8 is a transverse cross-sectional proximal end view of a primary catheter of a drainage catheter with retractable internal drains in accordance with an example embodiment with drain tubes in a deployed position.
FIG. 9 is a proximal end view of a central connecting piece of a drainage catheter with retractable internal drains in accordance with an example embodiment.
FIG. 9A is a transverse cross-sectional view taken along section line 9A-9A in FIG. 9 of a central connecting piece of a drainage catheter with retractable internal drains in accordance with an example embodiment.
FIG. 9B is a transverse cross-sectional view taken along section line 9B-9B in FIG. 9 of a central connecting piece of a drainage catheter with retractable internal drains in accordance with an example embodiment.
Figure 11:
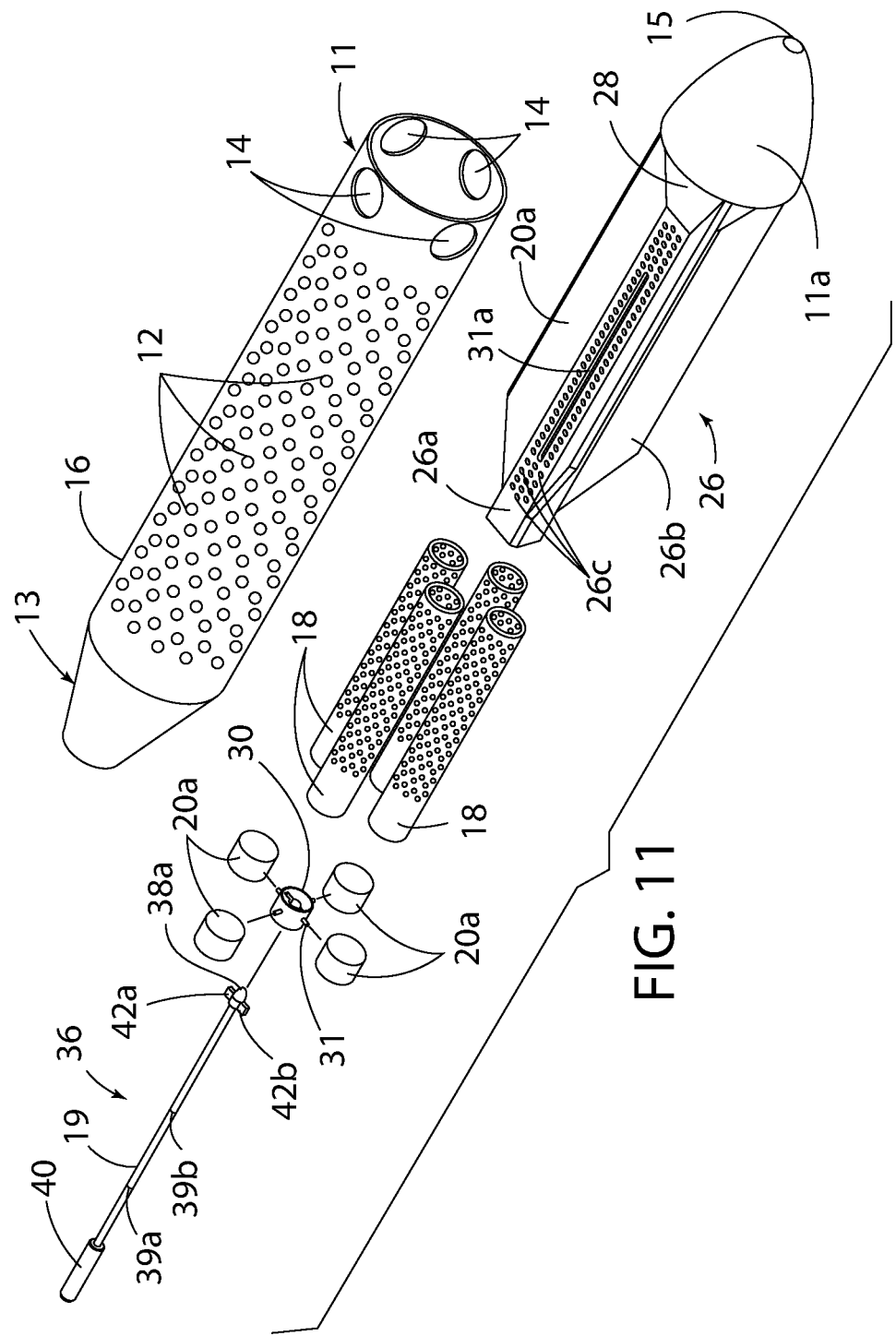
FIG. 11 is an exploded isometric view of a stylet and a drainage catheter with retractable internal drains in accordance with an example embodiment.
Figure 13:
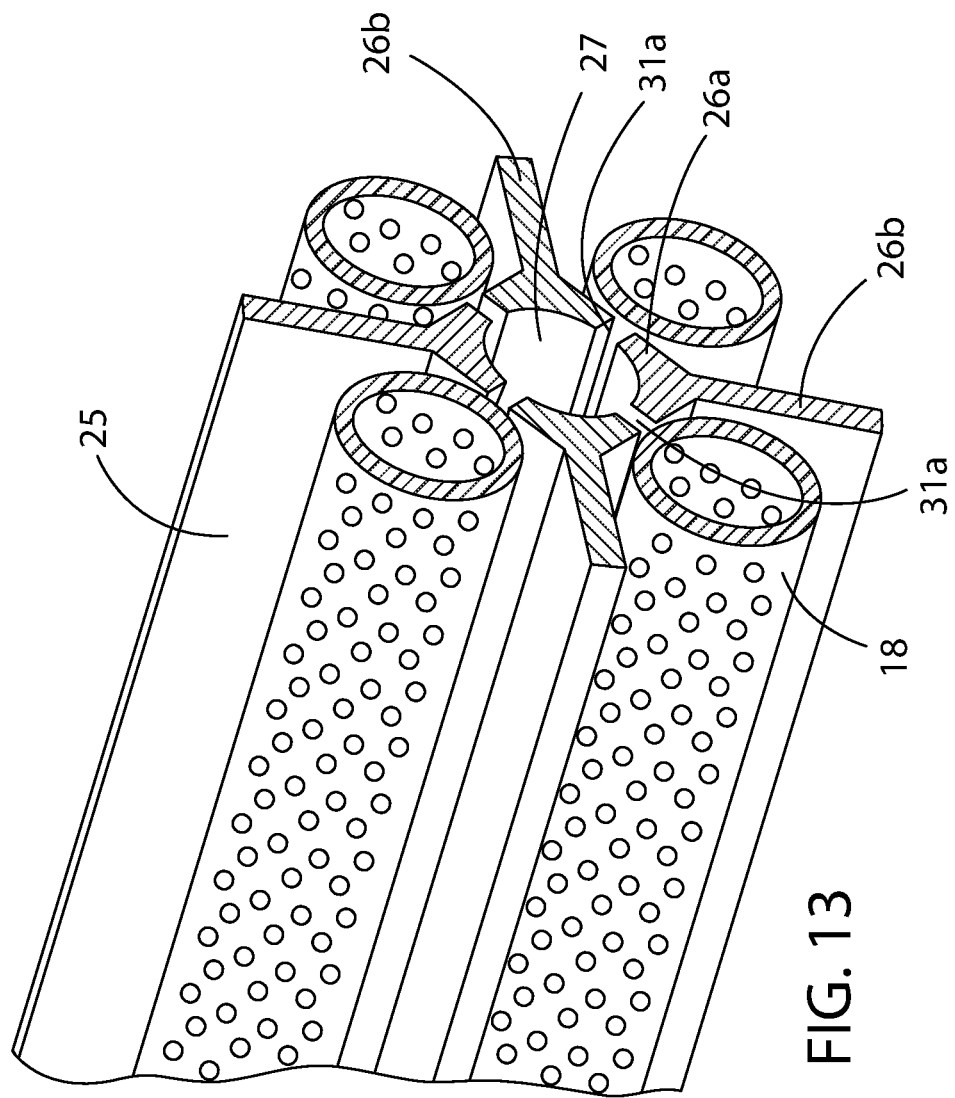
FIG. 13 is an isometric view showing portions of a track partition structure and internal drains of a drainage catheter with retractable internal drains in accordance with an example embodiment.

The central track 27 and peripheral tracks 25 are defined and separated by a longitudinal track partition structure 26, best illustrated in FIGS. 8, 11, and 13. In one embodiment illustrated in FIG. 6A, the track partition structure extends longitudinally and substantially coaxially with the primary catheter from a location proximate the internal drain ports 14 to a location proximate the junction of the distal 11 and proximal 13 ends of the primary catheter 10. At that location, the central track and lumen 27 and the peripheral tracks and lumens 25 all converge in a single draining lumen of the primary catheter proximal end 13. In another embodiment illustrated in FIG. 6B, the proximal end 13 of the primary catheter maintains the same diameter as the distal end 11, and the track partition structure, including the peripheral tracks and lumens 25, extend from a location proximate the internal drain ports 14 throughout the entire length of the primary catheter. The central and peripheral lumens defined by the central and peripheral tracks 25, 27 are thus adapted and function to conduct fluid flow between the distal and proximal ends 11, 13 of the primary catheter.

The track partition structure comprises a central portion 26a that is located substantially on the longitudinal axis of the primary catheter and a plurality of track walls 26b that extend radially outward from an outer surface of the central portion at evenly spaced intervals, and that terminate at an inner surface of the primary catheter body 16. A longitudinal opening in the central portion 26a extends the entire length of the track partition structure such that the central portion is open from end to end. The longitudinal opening defines the central track 27 and lumen. Each peripheral track 25 and lumen is defined as the space bounded by the outer surface of the central portion 26a, two adjacent track walls 26b, and the inner surface of the catheter body 16. It should be noted that while the central track and lumen are preferably cylindrical in shape, they could be formed in other shapes consistent with the purposes of slideably retaining a central connecting piece 30 described in further detail below.

Preferably the central portion 26a and track walls 26b have a plurality of fluid exchange openings or tracks 26c formed in them to facilitate the conduct of fluid flow and exchange between the peripheral and central lumens at a plurality of locations and along a plurality of routes. At the same time, the plurality of drain openings 12 in the primary catheter body 16 provide for fluid flow between the exterior of the primary catheter body and the central and peripheral lumens at a plurality of locations and via a plurality of routes.

Disposed within each of the plurality of peripheral tracks 25 is an internal retractable drain 18, which is described in further detail below. Generally, however, the plurality of retractable internal drains can be caused to assume a retracted state or position and a deployed state or position.

Figure 3:
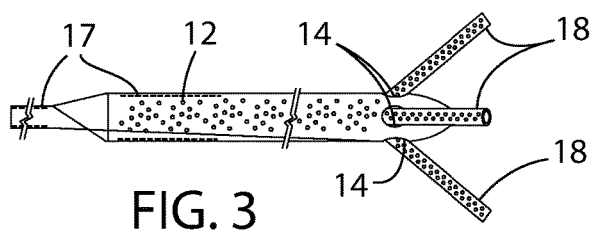
FIG. 3 is a partial side view of a drainage catheter with retractable internal drains in accordance with an example embodiment with drain tubes in a deployed position.
Figure 12:
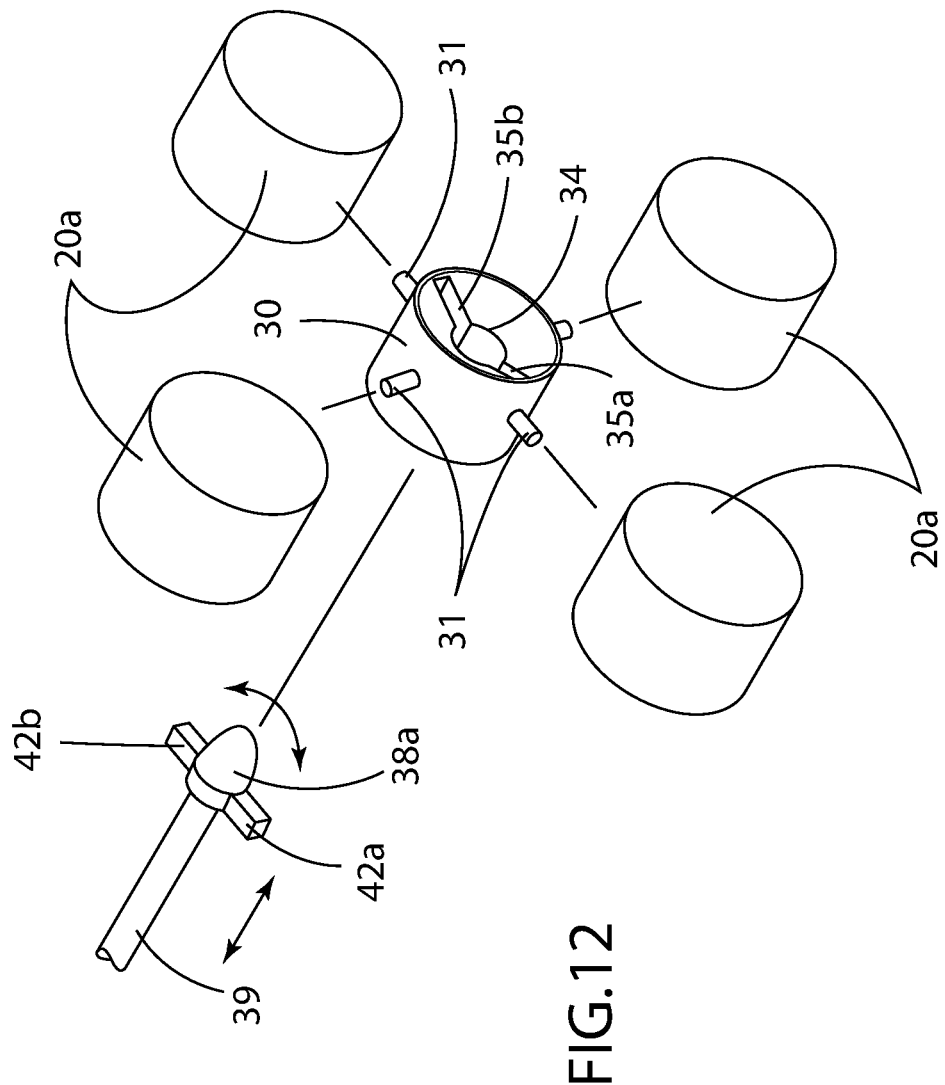
FIG. 12 is an exploded isometric view showing the tip portion of a stylet, together with a central connecting piece and portions of internal drains of a drainage catheter with retractable internal drains in accordance with an example embodiment.

In the retracted state, as shown in FIGS. 6A-6C for example, the plurality of drains are fully enclosed or contained within corresponding peripheral tracks 25. In the deployed state, as shown in FIGS. 3, 7, and 12 for example, the plurality of drains extend radially outwardly from the distal end 11 of the primary catheter through the internal drain ports 14. When the drains 18 are deployed, they remain in fluid communication with the peripheral lumens defined by the corresponding peripheral tracks 25. The deployed drains thus provide for fluid flow between the peripheral lumens and an additional plurality of locations exterior to the primary catheter and via an additional plurality of routes spread over an even larger area than occupied by the primary catheter itself.

From the foregoing descriptions, persons of skill in the art will appreciate that the example embodiment simultaneously provides substantially expanded drainage and irrigation area, promotes a substantial volume of fluid flow, provides the ability to conduct fluid flow to and from a plurality of locations simultaneously, provides a plurality of fluid flow routes, and reduces or prevents catheter blockage, among other benefits.

Also disposed within each of the plurality of peripheral tracks 25 is a drain deployment guide 28. Each drain deployment guide is located at the distal end of a corresponding peripheral track 25 proximate to the corresponding internal drain port 14. The drain deployment guides function to facilitate deployment of the internal drains 18 radially outwardly from the primary catheter through the internal drain ports 14. Each drain deployment guide comprises an angled or tilted surface that extends outwardly from the distal ends of the track walls 26b and the outer surface of the central portion 26a of the track partition structure 26 that define the corresponding peripheral track 25. The drain deployment guide extends toward the inner wall of the primary catheter body 16 and ends at the distal edge of the corresponding internal drain port 14. This configuration creates a ramp of sorts that guides an internal drain 18 during deployment through the internal drain port 14 and outwardly from the primary catheter approximately at the angle of the surface. Preferably the drain deployment guides 28 are formed of a material that is relatively more firm than the material of the retractable internal drains 18 so that the drains are apt to flex somewhat when moved into contact with the deployment guide during deployment. The drain deployment guides 28 suitably can take the form of a thin sheet of relatively stiff material or a solid triangular component as shown in FIGS. 6A-6C for example.

In operation, as an internal drain 18 moves toward the distal end 11 of the primary catheter during deployment, the inward distal edge of the drain contacts the leading edge of the angled surface of the corresponding drain deployment guide 28. This redirects the motion of the drain at an angle toward the corresponding internal drain port 14. Further motion of the drain then results in the drain passing through the internal drain port and outwardly from the primary catheter at approximately the angle of the angled surface as shown in FIGS. 3 and 7 for example.

Persons skilled in the art will appreciate that by choosing the angle of the angled surface and placement of the internal drain ports radially around the circumference of the distal end of the primary catheter, one can readily determine the configuration of the internal drains in the deployed state. Such persons also will understand that the angle of the angled wall and placement of the internal drain ports may vary depending on the particular application for which the catheter is intended, including the size and location or locations within a subject of an area to be drained or irrigated.

A relatively thick and/or stiff reinforcing structure or material 11b may be disposed within the distal end 11 of the primary catheter proximate to the catheter tip 11a to reinforce or provide additional rigidity to the catheter tip. This aids in inserting and guiding the primary catheter within a subject, and also reduces or prevents the risk of deformation of the primary catheter, for example if an obstruction is encountered. The reinforcing structure or material may comprise a solid silicon or polyurethane for example. As indicated above, in some embodiments the drain deployment guides 28 may be formed integrally with or may be connected to the reinforcing structure or material 11b. In addition, a funnel shaped guidewire guide 29 may be formed integrally with or attached to the reinforcing structure or material 11b adjacent to and just proximally of the guidewire port 15 in tip 11a to help direct a guidewire through the guidewire port.

C. Internal Retractable Drains.

Figure 4:
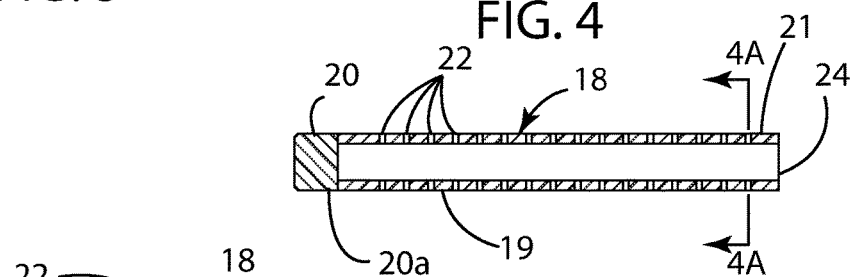
FIG. 4 is a partial side view of a retractable internal drain in accordance with an example embodiment.
Figure 4A:
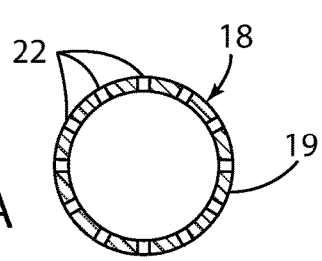
FIG. 4A is a transverse cross-sectional view taken along section line 4A-4A in FIG. 4 of a drain tube of a retractable internal drain in accordance with an example embodiment.

In one embodiment shown in FIGS. 4 and 4A, the retractable internal drain 18 comprises an elongated hollow tube 19 having a proximal end 20, a distal end 21 and a distal end tip 24. The distal end tip 24 may be tapered if desired. The tube 19 is open at both the proximal and distal ends. The tube is preferably formed of polyurethane or silicon and is relatively flexible. Those skilled in the art will understand that any number of other materials may also be used consistent with the intended function of the tube and intended applications of the catheter as described herein. Also depending on the intended application of the catheter and individual preference, the tube 19 can be formed in various shapes including a straight, curved, or coiled shape, such as a helix. Preferably, the tube includes multiple perforations 22 formed in and extending through its surface to facilitate liquid flow between the interior and exterior of the tube, in addition to fluid flow through the open proximal and distal ends. The tube can be selected to have a length within a range depending on the intended application and individual preference. However, the overall length of the tube should be limited so that in the retracted state the tube is fully enclosed within a corresponding peripheral track 25, as illustrated in FIGS. 6A-6C for example. Persons skilled in the art will appreciate that a coil-shaped tube can provide more overall tube length and thus drainage area in the deployed state compared to a straight tube while still being able to be fully enclosed within the same length peripheral track in the retracted state.

Figure 5:
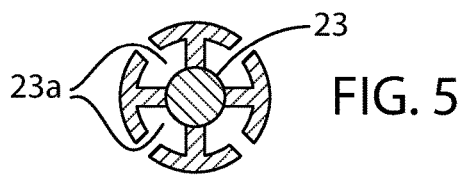
FIG. 5 is a transverse cross-sectional view of a drain structure of a retractable internal drain in accordance with another example embodiment.

In another embodiment shown in FIG. 5, the retractable internal drain is formed as an elongated central member 23 having a plurality of longitudinal grooves 23a radially spaced about its periphery and extending for the entire length of the member. This is similar to drain structures shown previously in U.S. Pat. Nos. 4,465,481 and 4,398,910, although those structures were not designed or intended to be retractable within a primary catheter. In this embodiment, fluid flow is conducted along and within the plurality of grooves 23a between distal and proximal ends of the elongated member 23, rather than through a single central lumen of a tube 19 as in the embodiment of FIGS. 4 and 4A.

In a preferred embodiment, the proximal end 20 of the drain 18 includes a reinforced base 20a comprised of a thicker and stiffer material than the remainder of the drain. The base functions to provide support for the remainder of the drain, which is formed of a somewhat softer and more flexible material, and to provide a solid connection point to the drain for the central connecting piece 30 described below to facilitate deployment and retraction of the drain. The base can be formed of the same material as the remainder of the drain, but with a thicker cross section for added stiffness. Alternatively, the base can be formed of a different and stiffer metallic material, such as titanium or a stainless steel alloy, or any other material that provides the desired stiffness and that is compatible with the material of the remainder of the drain. The base may be attached to, may envelope, or may be integrally formed with the proximal end of the drain in a suitable fashion, and may extend longitudinally for a selected distance along the length of the proximal end of the drain. However, the length of the base is preferably selected so that it does not substantially engage a corresponding drain deployment guide 28 and remains enclosed within the corresponding peripheral track 25 when the drains are deployed.

D. Central Connecting Piece.

A central connecting piece 30 is disposed within the central track 27 as illustrated in FIGS. 6A-6C, 7, and 8 for example. The central connecting piece preferably is formed of a solid, relatively rigid material, such as plastic or metal.

The central connecting piece is preferably formed in the shape of a cylindrical disk and is disposed within the central track substantially coaxially with the longitudinal axis thereof. The central connecting piece 30 is preferably dimensioned to freely slide within the central track 27 and along its longitudinal axis in the directions of the distal 11 and proximal 13 ends of the primary catheter. For example, FIGS. 6A-6C illustrate the central connecting piece 30 at a location within the central track 27 nearer the proximal end of the primary catheter while FIG. 7 illustrates the central connecting piece 30 at a location nearer the distal tip 11a of the primary catheter. While the central connecting piece and the central track are substantially cylindrical in cross-section in the example embodiment, those skilled in the art will appreciate that the central connecting piece and the central track could have an octagonal, square or other cross-sectional shape so long as the shape is consistent with providing the functionality described herein.

As illustrated in FIGS. 9, 9A, and 9B, as well as FIGS. 11-12, the central connecting piece 30 includes a central opening 34 substantially centered in the face of the central connecting piece and preferably substantially centered on the longitudinal axis of the primary catheter when the central connecting piece is disposed in the central track 27. The central opening 34 is preferably, but not necessarily, cylindrical in shape and defines a central channel for a guidewire (not shown) to pass through in either direction between the proximal and distal ends of the primary catheter. Preferably the central opening 34 is substantially coaxial with the guidewire port 15 in the distal tip 11a of the primary catheter. To facilitate passage of a guidewire through the central opening 34 in either direction, the central connecting piece 30 is formed with a funnel-shaped cross-section 33 at least in the areas adjacent to the central opening 34 on opposite distal and proximal faces of the central connecting piece.

The central connecting piece 30 also includes a pair of slots 35a, 35b extending laterally in opposite directions from the central opening 34. The slots have a thickness dimension less than the diameter of the central opening. The central opening 34 and slots 35a, 35b are intended to cooperate with a corresponding wing-shaped distal tip of a stylet 36 described in detail below to facilitate insertion and location of the primary catheter in a subject, and the deployment and retraction of internal drains 18 in a manner also described below.

Referring to FIGS. 6A-6C, 8, and 11-13, the central connecting piece 30 is connected in common with each of the plurality of internal drains 18 via connecting bars 31. The connecting bars have proximal ends connected to the central connecting piece and distal ends connected to the bases 20*a* of the internal drains 18. Preferably the connecting bars are formed of a relatively rigid material such as plastic or metal. The connecting bars 31 may be formed integrally with the central connecting piece 30 or may be separately formed and fixedly attached to the central connecting piece at their proximal ends. The connecting bars extend laterally outwardly from the outer edge of the central connecting piece 30 through slots 31*a* formed in the central portion 26*a* of the track partition structure 26 and connect at their distal ends to the bases 20*a* of the internal drains 18. Preferably the connecting bars are spaced radially around the circumference of the central connecting piece with each connecting bar located adjacent to the internal drain to which it connects. This configuration provides for common movement of all of the internal drains simultaneously and in the same direction in response to movement of the central connecting piece in the central track. The connecting bars may extend outwardly from the central connecting piece in a common plane with the central connecting piece as shown in FIGS. 6A, 6B, and 11-12. Alternatively, the connecting bars may extend outwardly from the central connecting piece at a forward angle toward the distal end of the primary catheter as shown in FIG. 6C.

A distal stop 32 and a proximal stop 33 are formed on the inner surface of the central portion 26*a* of the track partition structure 26, which defines the central track 27, to limit the extent of movement of the central connecting piece 30 toward the distal and proximal ends of the primary catheter respectively. The stops preferably are formed as annular or semi-annular ridges but can be formed in a variety of shapes including rods, cylinders or rings. The stops reduce the inner diameter of the central track where they are located to a diameter less than that of the central connecting piece, thereby preventing movement of the central connecting piece within the central track 27 beyond the stops. The location of the proximal stop 33 preferably defines and corresponds with the fully retracted position or state of the internal drains and the location of the distal stop 32 preferably defines and corresponds with the fully deployed position or state of the internal drains. Thus, the proximal stop 33 is positioned so that the central connecting piece engages it as the central connecting piece is moving toward the proximal end of the primary catheter and the internal drains are in a fully retracted position or state in which they are fully enclosed within the peripheral tracks 25. Similarly, the distal stop 32 is positioned so that the central connecting piece engages it as the central connecting piece is moving toward the distal end of the primary catheter and the internal drains are in a fully deployed position in which they extend radially outwardly from the distal end of the primary catheter through the internal drain ports 14. However, the distal stop 32 is further positioned so that when the central connecting piece engages it, the reinforced base portions 20*a* of the internal drains 18 remain enclosed within the peripheral tracks 25 and not in substantial engagement with the angled drain deployment guides 28 as shown in FIGS. 7 and 15 for example.

E. Stylet.

Figures 10, 10A:
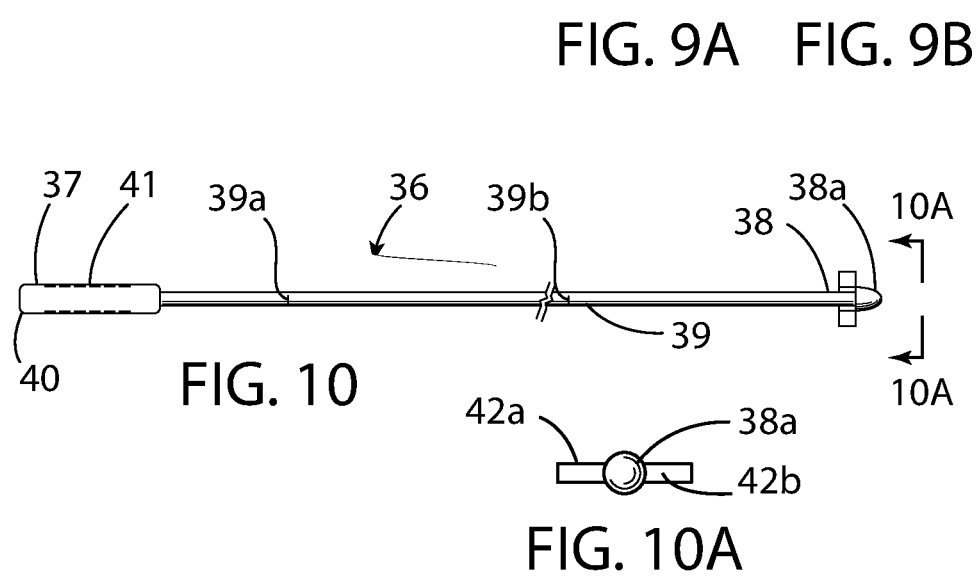
FIG. 10 is a partial side view of a stylet for use with a drainage catheter with retractable internal drains in accordance with an example embodiment.
FIG. 10A is a transverse cross-sectional view taken along section line 10A-10A in FIG. 10 of the distal tip of a stylet for use with a drainage catheter with retractable internal drains in accordance with an example embodiment.

A stylet 36 is employed for two main functions: to facilitate the insertion and location of the primary catheter 10 in a subject and to deploy or retract the internal drains 18. Referring primarily to FIGS. 10-12, the stylet has a proximal end 37 and a distal end 38 connected by a shaft 39. The shaft is suitably made of a relatively rigid material such as steel, or a somewhat more flexible material such as braided steel fibers, and may have various lengths depending on the dimensions of the primary catheter with which it is used and the distance to the location within a subject the primary catheter is to be positioned.

A pair of level indicators 39*a* and 39*b* are provided on the shaft 39. The level indicators are spaced apart longitudinally on the shaft at selected locations. The locations are selected to correspond to the distances the stylet must be inserted in and retracted from the primary catheter in engagement with the central connecting piece 30 for the internal drains 18 to be fully deployed (indicator 39*a*) and fully retracted (indicator 39*b*). The indicators thus facilitate engagement of the central connecting piece 30 by the stylet and deployment and retraction of the internal drains 18 as described in detail below. The indicators can take the form of painted points or bars, or alternatively can comprise grooves, indentations, or any other form that can provide a visual indication of the level of insertion of the stylet in the primary catheter. It will be apparent to persons skilled in the art that the selection of locations on the stylet for the level indicators will depend on a number of variables, including the relative length dimensions of the primary catheter, the stylet, and the internal drains 18, the desired distance for full deployment of the drains, and others. Thus, persons skilled in the art will appreciate that the locations at which the level indicators 39*a*, 39*b* are shown on the shaft 39 of stylet 36 in FIG. 10 are chosen merely to facilitate the foregoing discussion and do not represent any particular embodiment.

The proximal end 37 of the stylet 36 is provided with a handle 40 by which a user can manipulate the stylet, including inserting it into and retracting it from the proximal end 13 of the primary catheter, advancing and retracting it within the central track 27 of the primary catheter in the distal and proximal directions, and rotating it within the central track. The handle preferably has a diameter or width dimension greater than the diameter or width dimension of the opening in the proximal end of the primary catheter to prevent the handle from entering the primary catheter. Angular orientation indicators 41 are provided on opposing sides of the outside surface of the handle. The orientation indicators are preferably slits, although other indication mechanisms can be used. Alternatively or in addition, angular orientation indicators (not shown) could be provided on opposing sides of the stylet shaft 39 over the entire or a substantial portion of the length of the stylet if desired. The orientation indicators 41 function in cooperation with the orientation indicators 17 formed along the length of the exterior surface of the primary catheter body to visually indicate the angular orientation of the stylet relative to the primary catheter. By ensuring the orientation indicators 17 extend to portions of the primary catheter that extend outside the body of a subject in which the distal end of the primary catheter resides, the indicators 41 on the handle of the stylet can be visually aligned with the indicators 17 on the body of the primary catheter when the stylet 36 is inserted into the catheter. As described in detail below, this provides a visual indication when the stylet is angularly oriented within the primary catheter such that wing-shaped structures on the distal tip of the stylet are aligned with the central opening 34 and lateral slots 35a, 35b of the central connecting piece 30 so that the stylet can pass through rather than engage the central connecting piece.

The distal end 38 of the stylet has a distal tip 38a formed in a shape designed to cooperate with the central opening 34 and lateral slots 35a, 35b of the central connecting piece 30. The distal tip 38a includes a central section that is substantially cylindrical. Preferably the central section is substantially rounded off at the distal end as shown in FIGS. 10-12. The central section is dimensioned to have a maximum diameter that is less than the diameter of the central opening 34 in the central connecting piece 30 so that the distal tip 38a can fit within and pass through the central opening 34 when aligned with it. The distal tip 38a also has a pair of "wings" 42a and 42b that extend outwardly in opposite directions from opposite sides of the distal tip. The wings are radially spaced apart and are dimensioned such that when the stylet is angularly oriented within the central catheter with the wings 42a, 42b of the stylet distal tip 38a aligned with the slots 35a, 35b of the central connecting piece 30 and the central section of the distal tip 38a aligned with the central opening 34 of the central connecting piece 30, the distal tip 38a can pass through the central connecting piece in either direction. However, when the wings 42a, 42b of the stylet distal tip 38a are not aligned with the slots 35a, 35b of the central connecting piece 30, the distal tip 38a of the stylet cannot pass through the central connecting piece 30 in either direction but rather engages the central connecting piece.

To provide a visual indication and facilitate alignment of the distal tip 38a and central connecting piece 30, the orientation indicators 41 on the stylet handle 40 are angularly positioned relative to the wings 42a, 42b on stylet distal tip 38a and the orientation indicators on the body of the primary catheter are angularly positioned relative to the slots 35a, 35b of the central connecting piece 30 such that when the orientation indicators 41 and 17 are aligned, the wings 42a, 42b of the stylet distal tip 38a and slots 35a, 35b of the central connecting piece 30 are aligned. In the example embodiment in particular, the orientation indicators 41 are formed on the opposing surfaces of handle 40 that are substantially parallel with or that have tangents substantially parallel with the wings 42a, 42b of the stylet distal tip 38a. Similarly, the orientation indicators 17 are formed on the opposing exterior surfaces of the primary catheter body that are substantially parallel with or that have tangents substantially parallel with the slots 35a, 35b of the central connecting piece 30.

It will be apparent to persons skilled in the art that numerous alternative alignment mechanisms can also be used. For example, the stylet distal tip can have more than two wings and the central connecting piece more than two corresponding slots. Further, the wings and corresponding slots may be arranged in a variety of configurations. For example, the wings and corresponding slots may be angularly spaced and extend outwardly from corresponding central points. Alternatively, the distal tip of the stylet may be formed in a star or other geometric shape and the openings in the central connecting piece may be formed in corresponding shapes. Essentially, the stylet distal tip and the corresponding openings of the central connecting piece can be selected to have nearly any shape that will permit the stylet distal tip to pass through the central connecting piece in a particular angular orientation and to be blocked from passing through in other angular orientations.

The configuration of the stylet distal tip 38a facilitates insertion of the primary catheter 10 through body tissue or a tract of a subject by permitting the stylet 36 to be advanced through the central connecting piece 30 until the distal tip 38a reaches the funnel shaped guidewire guide 29 at the primary catheter tip 11a as shown in FIG. 14. The substantially rounded end of the distal tip 38a engages with the sloped surfaces of the guidewire guide 29 and further advancement of the stylet 36 then advances the primary catheter tip 11a forward for insertion and location of the primary catheter 10 within the subject.

The configuration of the stylet distal tip 38a also facilitates deployment and retraction of the internal drains 18. For deployment, the stylet 36 is inserted into the proximal end 13 of the primary catheter 10 and is advanced within the central track 27 toward the distal tip 11a. The stylet is angularly rotated so that the wings 42a, 42b of the stylet distal tip 38a are not aligned with the slots 35a, 35b of the central connecting piece 30. Since the stylet distal tip 38a is unable to pass through the central connecting piece 30 in that state, further advancement of the stylet pushes the central connecting piece 30 and the commonly connected internal drains 18 toward the distal tip 11a of the primary catheter within the central 27 and peripheral 25 tracks respectively. As the internal drains 18 advance toward the distal tip 11a of the primary catheter 10, the distal tips 24 of the drains 18 engage the drain deployment guides 28 and are directed radially outwardly from the primary catheter through the internal drain ports 14. Further advancement of the stylet 36 continues to push the central connecting piece 30 toward the distal tip 11a of the primary catheter until the central connecting piece engages the distal stop 32. At that point, the internal drains 18 are fully deployed as shown in FIG. 15.

To retract the internal drains 18, the stylet 36 is angularly rotated until the wings 42a, 42b of the stylet distal tip 38a are aligned with the slots 35a, 35b of the central connecting piece 30 as visually indicated by the orientation indicators 16, 37 on the stylet handle 40 and primary catheter body 16 respectively. With the wings 42a, 42b and slots 35a, 35b aligned, the stylet can be advanced toward the distal tip 11a of the primary catheter and the distal tip 38a of the stylet can pass through the central connecting piece 30. The stylet can then be rotated so that the wings 42a, 42b and slots 35a, 35b are no longer aligned and then be retracted toward the proximal end 13 of the primary catheter. Because the wings 42a, 42b and slots 35a, 35b are not aligned, the stylet distal tip 38a engages the central connecting piece 30 as it is retracted and causes the central connecting piece to slide toward the proximal end 13 of the primary catheter. This in turn causes the commonly connected internal drains 18 to retract through the internal drain ports 14 and into the peripheral tracks 25. As the stylet 36 continues to be retracted, the central connecting piece 30 continues to slide toward the proximal end 13 of the primary catheter until the central connecting piece engages the proximal stop 33. At that point, the internal drains 18 are fully retracted as shown in FIGS. 6A-6C and 14. The stylet can then be fully retracted from the primary catheter by rotating it until the wings 42a, 42b and slots 35a, 35b are aligned and then retracting the stylet until the stylet distal tip 38a passes through the central connecting piece 30 and out the proximal end 13 of the primary catheter.

F. Multiple Sets of Retractable Drains.

FIGS. 16 and 17 illustrate an example drainage catheter with retractable internal drains having more than one set of internal drains. In this example embodiment, the primary catheter 10 has a first set of internal drains 43 and a second set of internal drains 44 longitudinally spaced within the primary catheter.

The primary catheter has a central track 27 and peripheral tracks 25 defined and separated by a track partition structure 26 as described above. The central and peripheral tracks are arranged within the primary catheter in the same manner as described above.

The first and second sets of internal drains 43, 44 are disposed within the peripheral tracks 25 essentially as described above with respect to the internal drains 18 except that two internal drains 43, 44 are longitudinally spaced in each peripheral track 25 instead of one internal drain 18. Each of the internal drains of the first and second sets is essentially the same in construction and function as the internal drains 18 described previously.

A first set of internal drain ports 45 is formed in the distal end 11 of the primary catheter through which the first set of internal drains 43 can be deployed and retracted in the same manner described previously with respect to drains 18. A second set of internal drain ports 46 is formed in the distal end 11 of the primary catheter through which the second set of internal drains 44 can be deployed and retracted also in the same manner described previously with respect to drains 18. The first and second sets of internal drain ports 45, 46 are longitudinally spaced on the primary catheter corresponding with the longitudinal spacing of the first and second sets of internal drains 43, 44. A first set of drain deployment guides 47 is positioned proximate to the first set of drain ports 45 and a second set of drain deployment guides 48 is positioned proximate to the second set of drain ports 46. The first and second sets of drain deployment guides 47, 48 are arranged, constructed, and function in the same manner as the drain deployment guides 28 described previously to facilitate deployment of the first and second sets of internal drains 43, 44 through the corresponding first and second sets of drain ports 45, 46.

A first central connecting piece 49 and a second central connecting piece 50 are disposed within and longitudinally spaced in the central track 27 corresponding to the longitudinal spacing of the first and second sets of internal drains 43, 44. Both of the first and second central connecting pieces 49, 50 are constructed and function the same as the central connecting piece 30 as described above. The first central connecting piece 49 commonly connects the drains of the first set of internal drains 43 and the second central connecting piece 50 commonly connects the drains of the second set of internal drains 44 in the same manner as central connecting piece 30 commonly connects drains 18.

A first distal stop 51 is formed on the inner surface of the central track 27 the same as previously described with respect to distal stop 32. The first distal stop 51 functions the same as previously described with respect to distal stop 32 to prevent further motion of the first central connecting piece 49 toward the distal tip 11a of the primary catheter once the first set of internal drains 43 are fully deployed. In this example embodiment, the second set of drain deployment guides 48 serve as a proximal stop with respect to the first set of internal drains 43. The drain deployment guides 48 are positioned in the peripheral tracks 25 so as to engage the bases 20a of the first set of internal drains 43 and prevent further motion of the drains and the commonly connected first central connecting piece 49 toward the proximal end 13 of the primary catheter once the first set of internal drains 43 are fully retracted into the peripheral tracks 25. A second distal stop 52 and a second proximal stop 53 are formed on the inner surface of the central track 27 the same as previously described with respect to distal stop 32 and proximal stop 33. The second distal stop 52 functions the same as previously described with respect to distal stop 32 to prevent further motion of the second central connecting piece 50 toward the distal tip 11a of the primary catheter once the second set of internal drains 44 are fully deployed. The second proximal stop 53 functions the same as previously described with respect to proximal stop 33 to prevent further motion of the second central connecting piece 50 toward the proximal end 13 of the primary catheter once the second set of internal drains 44 are fully retracted.

Stylet 36 is useable with respect to this example embodiment to insert and locate the primary catheter within a subject and to deploy and retract the drains in the same manner as described above, but with minor variations that are apparent to account for the presence of two longitudinally spaced central connecting pieces 49, 50 and longitudinally spaced first and second sets of internal drains 43, 44. For example, to insert and locate the primary catheter within a subject, the stylet 36 is inserted in the proximal end 13 of the primary catheter, is rotated to align the wings 42a, 42b of stylet distal tip 38a with the slots 35a, 35b in the second central connecting piece 50, and is advanced until the distal tip 38a passes through the second central connecting piece 50. The stylet is then further rotated to align the wings 42a, 42b of the stylet distal tip 38a with the slots 35a, 35b in the first central connecting piece 49 and is advanced so that the stylet distal tip 38a passes through the first central connecting piece 49 and comes into engagement with the distal tip 11a of the primary catheter to facilitate insertion and location within the subject.

Another variation is that in this embodiment, the first and second sets of internal drains 43, 44 can be independently deployed and retracted. To deploy the first set of drains, the stylet 36 is inserted in the proximal end 13 of the primary catheter and the same process described above is followed to advance the stylet distal tip 38a through the second central connecting piece 50. However, rather than orienting the stylet so the distal tip 38a passes through the first central connecting piece 49, the stylet is rotated so the stylet distal tip 38a engages the first central connecting piece. Then, further advancing the stylet toward the distal tip 11a of the primary catheter until the first central connecting piece 49 abuts the first distal stop 51 fully deploys the first set of drains 43 in the same manner as previously described with respect to deploying drains 18. To retract the first set of drains 43, the stylet is rotated so the wings 42a, 42b of the stylet distal tip 38a are aligned with the slots 35a, 35b in the first central connecting piece 49 and the stylet is then advanced until the distal tip 38a passes through the first central connecting piece 49. The stylet is then rotated again so the wings 42a, 42b of the stylet distal tip 38a are not aligned with the slots 35a, 35b in the first central connecting piece 49 and the stylet is retracted causing the stylet distal tip 38a to engage the first central connecting piece 49. The stylet is then retracted until the bases 20a of the first set of internal drains 43 abut the second set of drain deployment guides 48. At that point, the first set of internal drains 43 is fully retracted. To fully retract the stylet from the primary catheter the stylet is alternately rotated and retracted so that the wings 42a, 42b of the stylet distal tip 38a align with the slots 35a, 35b of each of the first and second central connecting pieces 49, 50 and the stylet distal tip 38a passes through each of the first and second central connecting pieces 49, 50 successively and then exits the proximal end 13 of the primary catheter.

The second set of internal drains 44 are similarly deployed and retracted independently from the first set of internal drains 43 by alternately rotating and advancing or retracting the stylet as described above so the wings 42a, 42b of stylet distal tip 38a align with the slots 35a, 35b of the second central connecting piece 50 and the stylet distal tip 38a passes through the second connecting piece, or the stylet distal tip 38a engages the second central connecting piece 50 in the same manner as described above.

It will be apparent to persons of ordinary skill in the art that in this example embodiment, when both sets of drains are fully deployed, they form a branching tree-like structure which provides an even wider surface area for drainage and irrigation and even more fluid flow paths than a single set of internal drains. This in turn maximizes fluid flow volume, enables fluid flow to or from even more locations, and further minimizes the risk of catheter blockage.

G. Operation of Preferred Embodiment.

Use of an example embodiment embodying the invention is described with reference to FIGS. 18 and 19.

FIG. 18 illustrates an example embodiment integrated within a ventriculoperitoneal shunt system. The ventricle 54 is a cavity within the brain 55 that is naturally filled with cerebrospinal fluid 56. However, an excess accumulation of cerebrospinal fluid can lead to a condition known as hydrocephalus. To drain excess cerebrospinal fluid from an affected ventricle, the stylet 36 is used in the manner described hereinabove to insert the primary catheter 10 into the ventricle. The primary catheter 10 may be inserted through a burr hole drilled in the skull of the subject and advanced through the subject's brain tissue until the entire distal end 11 resides within the ventricle 54. Once the distal end is located within the ventricle, the stylet is used in the manner described previously to deploy the internal drains 18 within the ventricle cavity. The proximal end 13 of the primary catheter traverses the brain and is connected to a valve 57 that functions to regulate fluid drainage pressure. The valve is in turn connected to a shunt catheter 58 that typically is routed to the subject's peritoneal cavity.

Opening the valve 57 allows the excess cerebrospinal fluid to flow from the subject's ventricle into the interior of the distal end of the primary catheter not only through the open distal tips 24 of the deployed internal drains, but also through the perforations 22 in the internal drains and the drain openings 12 in the primary catheter body 16. The fluid entering the primary catheter flows from the distal end of the primary catheter to the proximal end through the central and peripheral lumens defined by the central and peripheral tracks 25, 27. The fluid also flows between the peripheral and central lumens through the fluid exchange openings 26c in the track partition structure 26. From the proximal end of the primary catheter, the fluid flows through the valve 57 and shunt catheter 58 to the subject's peritoneal cavity, from which it can be drained or absorbed in the subject's blood stream.

FIG. 19 illustrates an example embodiment integrated within a peritoneal dialysis system. In peritoneal dialysis, the dialysis fluid is introduced from outside a subject's body into the subject's peritoneal cavity 59 via a catheter. During a prescribed dwell time, fluids and waste products pass from the subject's bloodstream into the dialysis fluid. At the end of the dwell time, the dialysis fluid containing the waste products is allowed to drain from the peritoneal cavity through the catheter.

Referring to FIG. 16, the stylet 36 is used in the manner described hereinabove to insert the primary catheter 10 into the subject's peritoneal cavity 59. The primary catheter 10 may be inserted into the subject through an incision near the subject's umbilicus and advanced through the subject's abdominal wall 60 until the entire distal end 11 resides within the peritoneal cavity. Once the distal end is located within the peritoneal cavity, the stylet is used in the manner described previously to deploy the internal drains 18. The internal drains 18 can be deployed to spread to different spaces within the peritoneal cavity. The proximal end 13 of the primary catheter has an extended tunneled part 61 that passes through the incision and the subject's abdominal wall 60 and connects with the distal end 11 inside the peritoneal cavity. A cuff 62 can be positioned around the outer surface of the tunneled part 61, preferably within the abdominal wall 60. The cuff is made of non-absorbable fibers that promote tissue fibrosis and adhesion formation in order to help hold the catheter in place for a potentially lengthy period of time. Outside the subject's body the tunneled part 61 of the proximal end 13 is connected to peritoneal dialysis tubing 63 via an adapter 64.

Once the peritoneal dialysis system is in place, dialysis fluid can be introduced into and drained from the subject's peritoneal cavity through the primary catheter 10. The dialysis fluid flows between the subject's peritoneal cavity and the interior of the distal end of the primary catheter not only through the open distal tips 24 of the deployed internal drains 18, but also through the perforations 22 in the drain tubes and the drain openings 12 in the primary catheter body 16. Fluid within the primary catheter flows between the distal and proximal ends through the central and peripheral lumens defined by the central and peripheral tracks 25, 27. The fluid also flows between the peripheral and central lumens through the fluid exchange openings 26a in the track partition structure 26. During introduction of dialysis fluid into the peritoneal cavity, the fluid is introduced into and flows through the peritoneal dialysis tubing and the proximal end of the catheter, including the tunneled part, into the distal end of the catheter and through the aforementioned plurality of lumens and openings into the subject's peritoneal cavity. After the prescribed dwell period, the dialysis fluid is drained from the peritoneal cavity through the same plurality of openings into the distal end of the primary catheter, through the same plurality of lumens from the distal end to the proximal end of the catheter, and then through the dialysis tubing into a drain or container for disposal.

Unless otherwise defined, all technical and scientific terms used herein have the same meaning as commonly understood by one of ordinary skill in the art to which this invention belongs. Although specific terms are employed herein, they are used in a generic and descriptive sense only and not for purposes of limitation. All publications, patent applications, patents, and other references mentioned herein are incorporated by reference in their entirety to the extent allowed by applicable law and regulations. Any and all headings within the foregoing description are included for convenience only and have no limiting effect.

The drainage catheter with retractable internal drains may be embodied in other specific forms without departing from the spirit or essential attributes thereof, and it is therefore desired that the present embodiment be considered in all respects as illustrative and not restrictive. Many modifications and other embodiments of the drainage catheter with retractable internal drains will come to mind to one skilled in the art to which this invention pertains and having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although methods and materials similar to or equivalent to those described herein can be used in the practice or testing of the drainage catheter with retractable internal drains, suitable methods and materials are described above. Thus, the drainage catheter with retractable internal drains is not intended to be limited to the embodiments shown, but is to be accorded the widest scope consistent with the principles and features disclosed herein.

What is claimed is:

1. A catheter for fluid drainage or irrigation, comprising:
a primary catheter having a proximal end adapted for connection to a fluid drainage or irrigation source, a distal end adapted for insertion within a subject, a first lumen providing a first fluid flow path adapted to conduct a fluid between the proximal and distal ends, and a plurality of second lumens providing a plurality of second fluid flow paths adapted to conduct the fluid;
wherein the first lumen and the plurality of second lumens are in fluid communication by at least one channel radially extending between the first lumen and the plurality of second lumens;
a plurality of drain ports located in the distal end of the primary catheter; and
a plurality of drains in fluid communication with the plurality of second lumens, wherein the plurality of drains are selectively retractable and deployable, and wherein the plurality of drains are enclosed within the primary catheter in a retracted state and extend outwardly from the primary catheter through the plurality of drain ports in a deployed state;
whereby when the catheter is inserted into the subject and the plurality of drains are in the deployed state, the fluid can be conducted by the proximal end of the primary catheter and the plurality of drains.

2. The catheter of claim 1, wherein the plurality of drains comprise a plurality of elongated open-ended drain tubes.

3. The catheter of claim 1, wherein the plurality of drains are enclosed within the plurality of second lumens in the retracted state and extend outwardly from the plurality of second lumens through the plurality of drain ports in the deployed state.

4. The catheter of claim 3, wherein the first lumen and the plurality of second lumens are located within the primary catheter and the plurality of second lumens are spaced around the first lumen.

5. The catheter of claim 4, wherein the primary catheter comprises a common drain connector and wherein each of the plurality of drains is connected in common to the common drain connector.

6. The catheter of claim 5:
wherein the common drain connector is selectively movable between a first proximal position and a second distal position within the primary catheter; and
wherein in the first proximal position the plurality of drains are in the retracted state, and in the second distal position the plurality of drains are in the deployed state.

7. The catheter of claim 6, wherein the common drain connector is disposed within the first lumen.

8. The catheter of claim 7, wherein the primary catheter has a distal end tip, wherein the plurality of second lumens each have a proximal end and a distal end located near the distal end tip of the primary catheter, and wherein the plurality of drain ports are radially spaced about the primary catheter adjacent to the distal ends of the plurality of second lumens.

9. The catheter of claim 8, wherein the primary catheter comprises a plurality of drain deployment guides with each drain deployment guide of the plurality of drain deployment guides positioned between the distal end of a second lumen of the plurality of second lumens and a drain port of the plurality of drain ports to guide a drain of the plurality of drains radially outwardly through a drain port of the plurality of drain ports at an angle with respect to the primary catheter.

10. The catheter of claim 9, comprising:
an elongated stylet having a proximal end, a distal end, and a distal end tip, wherein the stylet is adapted to be inserted in the primary catheter and the distal end tip of the stylet moved between the proximal and distal ends of the primary catheter;
wherein the distal end tip of the stylet is adapted to selectively engage the common drain connector to selectively move the common drain connector to the first proximal position to place the plurality of drains in the retracted state and to the second distal position to place the plurality of drains in the deployed state.

11. The catheter of claim 10, wherein:
the distal end tip of the stylet is angularly rotatable;
the common drain connector has an opening; and
the opening is adapted to allow the distal end tip to pass through without engaging the common drain connector when the distal end tip is in a predetermined angular orientation with respect to the opening and for the distal end tip to engage the common drain connector without passing through the opening when the distal end tip is not in the predetermined angular orientation with respect to the opening.

12. The catheter of claim 11, wherein:
the distal end tip of the stylet comprises at least one projection; and
the opening in the common drain connector includes at least one portion adapted to receive the at least one projection and to allow the at least one projection to pass through without engaging the common drain connector when the distal end tip is in an angular orientation with respect to the opening such that the at least one projection is aligned with the at least one portion of the opening.

13. The catheter of claim 1, wherein the primary catheter comprises a body with an exterior and an interior, wherein the first lumen and the plurality of second lumens are disposed within the interior, and wherein the body has a plurality of drain openings providing a plurality of third fluid flow paths to conduct the fluid between the exterior of the primary catheter and the first lumen and plurality of second lumens.

14. The catheter of claim 1, wherein the plurality of drains comprise a plurality of elongated drain tubes, wherein the drain tubes have an interior with open ends, and an exterior surface, and wherein the exterior surface has a plurality of perforations in addition to the open ends to conduct the fluid between the interior and exterior of the drain tubes.

15. The catheter of claim 1, wherein the plurality of drains comprise a plurality of elongated solid members with proximal and distal ends, peripheral surfaces between the proximal and distal ends, and a plurality of elongated grooves formed in the peripheral surfaces for conducting the fluid between the proximal and distal ends.

16. The catheter of claim 1, wherein the distal end tip of the primary catheter has a guidewire port adapted for a guidewire to pass through for guiding the primary catheter into the subject.

17. A catheter for fluid drainage or irrigation, comprising:
a primary catheter having a proximal end adapted for connection to a fluid drainage or irrigation source, a distal end adapted for insertion within a subject, a first lumen providing a first fluid flow path adapted to conduct a fluid between the proximal and distal ends, and a plurality of second lumens providing a plurality of second fluid flow paths adapted to conduct the fluid;

wherein the first lumen and the plurality of second lumens are in fluid communication by at least one channel radially extending between the first lumen and the plurality of second lumens;

a plurality of first drain ports located in the distal end of the primary catheter;

a plurality of second drain ports located in the distal end of the primary catheter and longitudinally spaced apart from the plurality of first drain ports;

a plurality of first drains in fluid communication with the plurality of second lumens, wherein the plurality of first drains are selectively retractable and deployable, and wherein the plurality of first drains are enclosed within the primary catheter in a retracted state and extend outwardly from the primary catheter through the plurality of first drain ports in a deployed state; and a plurality of second drains in fluid communication with the plurality of second lumens and longitudinally spaced apart from the plurality of first drains, wherein the plurality of second drains are selectively retractable and deployable independently of the plurality of first drains, and wherein the plurality of second drains are enclosed within the primary catheter in a retracted state and extend outwardly from the primary catheter through the plurality of second drain ports in a deployed state;

whereby when the catheter is inserted into the subject and the plurality of first and second drains are in the deployed state, the fluid can be conducted by the proximal end of the primary catheter and the plurality of first and second drains.

18. The catheter of claim 17, wherein the plurality of first and second drains comprise a plurality of elongated open-ended drain tubes.

19. The catheter of claim 17, wherein the plurality of first drains are enclosed within the plurality of second lumens in the retracted state and extend outwardly from the plurality of second lumens through the plurality of first drain ports in the deployed state.

20. The catheter of claim 19, wherein the first lumen and the plurality of second lumens are located within the primary catheter and the plurality of second lumens are spaced around the first lumen.

21. The catheter of claim 20:
wherein the primary catheter comprises:
a first common drain connector, wherein each of the plurality of first drains is connected in common to the first common drain connector; and
a second common drain connector longitudinally spaced from the first common drain connector, wherein each of the plurality of second drains is connected in common to the second common drain connector.

22. The catheter of claim 21:
wherein the first common drain connector is selectively and independently movable between a first proximal position and a second distal position within the primary catheter, and the second common drain connector is selectively and independently movable between a third proximal position and a fourth distal position within the primary catheter; and
wherein in the first proximal position the plurality of first drains are in the retracted state, in the second distal position the plurality of first drains are in the deployed state, in the third proximal position the plurality of second drains are in the retracted state, and in the fourth distal position the plurality of second drains are in the deployed state.

23. The catheter of claim 22, wherein the first and second common drain connectors are disposed within the first lumen.

24. The catheter of claim 23:
wherein the primary catheter has a distal end tip;
wherein the plurality of second lumens each have a proximal end and a distal end located near the distal end tip of the primary catheter;
wherein the plurality of first drain ports are radially spaced about the primary catheter adjacent to the distal ends of the plurality of second lumens; and
wherein the plurality of second drain ports are radially spaced about the primary catheter at a location longitudinally spaced from the plurality of first drain ports and intermediate the proximal end and distal end tip of the primary catheter.

25. The catheter of claim 22, comprising:
an elongated stylet having a proximal end, a distal end, and a distal end tip, wherein the stylet is adapted to be inserted in the primary catheter and the distal end tip moved between the proximal end of the primary catheter and the distal end of the primary catheter;
wherein the distal end tip is adapted to selectively independently engage or pass through the first common drain connector and the second common drain connector;
wherein when the distal end tip is engaged with the first common drain connector, the stylet is operative to move the first common drain connector to the first proximal position to place the first plurality of drains in the retracted state and to the second distal position to place the first plurality of drains in the deployed state;
wherein when the distal end tip is engaged with the second common drain connector, the stylet is operative to move the second common drain connector to the third proximal position to place the first plurality of drains in the retracted state and to the fourth distal position to place the second plurality of drains in the deployed state;
wherein when the distal end tip passes through the first common drain connector and the second common drain connector, the stylet is operative to engage the distal end of the primary catheter for insertion of the primary catheter within the subject.

26. The catheter of claim 25, wherein:
the distal end tip of the stylet is angularly rotatable;
the first common drain connector has a first opening;
the second common drain connector has a second opening;
the first opening is configured to allow the distal end tip to pass through without engaging the first common drain connector when the distal end tip is in a first predetermined angular orientation with respect to the first opening and for the distal end tip to engage the first common drain connector without passing through the first opening when the distal end tip is not in the first predetermined angular orientation with respect to the first opening; and
the second opening is configured to allow the distal end tip to pass through without engaging the second common drain connector when the distal end tip is in a second predetermined angular orientation with respect to the second opening and for the distal end tip to engage the second common drain connector without passing through the opening when the distal end tip is not in the second predetermined angular orientation with respect to the second opening.

27. The catheter of claim 26, wherein:
the distal end tip of the stylet comprises at least one outward projection; and
the first opening in the first common drain connector and the second opening in the second common drain connector each include at least one portion configured to allow the at least one outward projection to pass through when the at least one outward projection is aligned with the at least one portion.

28. A catheter for fluid drainage or irrigation, comprising:
a primary catheter having a proximal end with an opening connectable to a drainage fluid container or a source of irrigation fluid, a distal end adapted for insertion within a subject, a first lumen providing a first fluid flow path adapted to conduct a fluid between the proximal and distal ends, and a plurality of second lumens providing a plurality of second fluid flow paths adapted to conduct the fluid, wherein the first lumen and the plurality of second lumens are in fluid communication by at least one channel between the first lumen and the plurality of second lumens;
a plurality of drain ports located in the distal end of the primary catheter;
a plurality of drains in fluid communication with the plurality of second lumens, wherein the plurality of drains are selectively retractable and deployable, and wherein the plurality of drains are enclosed within the primary catheter in a retracted state and extend outwardly from the primary catheter through the plurality of drain ports in a deployed state;
a common drain connector, wherein each of the plurality of drains is connected in common to the common drain connector, wherein the common drain connector is selectively movable between a first proximal position and a second distal position within the primary catheter, and wherein in the first proximal position the plurality of drains are in the retracted state, and in the second distal position the plurality of drains are in the deployed state; and
an elongated stylet having a proximal end, a distal end, and a distal end tip, wherein the stylet is adapted to be inserted in the primary catheter with the distal end tip movable between the proximal and distal ends of the primary catheter, and wherein the distal end tip is angularly rotatable and comprises at least one projection;
wherein the common drain connector has an opening with at least one portion having a shape corresponding to the at least one projection of the distal end tip of the stylet so that the distal end tip may selectively pass through the common drain connector when the distal end tip is in a predetermined angular orientation with the at least one projection and the at least one portion of the opening aligned, and may selectively engage the common drain connector when the distal end tip is not in the predetermined angular orientation and the at least one projection and the at least one portion of the opening are not aligned;
wherein when the distal end tip is engaged with the common drain connector, the stylet may be used to move the common drain connector to the first proximal position to place the plurality of drains in the retracted state and to the second distal position to place the plurality of drains in the deployed state, and wherein when the distal end tip passes through the common drain connector, the stylet may be used to engage the distal end of the primary catheter for insertion of the primary catheter within the subject.

29. The catheter of claim 28, wherein the opening in the common drain connector comprises a slot and the at least one projection of the distal end tip of the stylet comprises a wing.

30. The catheter of claim 28, wherein:
the common drain connector has a proximal side and a distal side with the proximal side being closer to the proximal end of the primary catheter than the distal end of the primary catheter, and the distal side being closer to the distal end of the primary catheter than the proximal end of the primary catheter;
the opening in the common drain connector is between the proximal and distal sides;
the proximal side of the common drain connector is engageable by the distal end tip of the stylet to push the common drain connector from the first proximal position to the second distal position to place the plurality of drains in the deployed state; and
the distal side of the common drain connector is engageable by the distal end tip of the stylet to pull the common drain connector from the second distal position to the first proximal position to place the plurality of drains in the retracted state.

31. A catheter for fluid drainage or irrigation, comprising:
a primary catheter having a proximal end adapted for connection to a fluid drainage or irrigation source, a distal end adapted for insertion within a subject, a first lumen providing a first fluid flow path adapted to conduct a fluid between the proximal and distal ends, and a plurality of second lumens providing a plurality of second fluid flow paths adapted to conduct the fluid;
wherein the first lumen and the plurality of second lumens are in fluid communication by at least two channels between the first lumen and the plurality of second lumens;
a plurality of drain ports located in the distal end of the primary catheter; and
a plurality of drains in fluid communication with the plurality of second lumens, wherein the plurality of drains are selectively retractable and deployable, and wherein the plurality of drains are enclosed within the primary catheter in a retracted state and extend outwardly from the primary catheter through the plurality of drain ports in a deployed state;
whereby when the catheter is inserted into the subject and the plurality of drains are in the deployed state, the fluid can be conducted by the proximal end of the primary catheter and the plurality of drains.

* * * * *